United States Patent
Moineau et al.

[11] Patent Number: 5,814,499
[45] Date of Patent: Sep. 29, 1998

[54] DNA ENCODOING PHAGE ABORTIVE INFECTION PROTEIN FROM LACTOCOCCUS LACTIS AND METHOD OF USE THEREOF

[75] Inventors: Sylvain Moineau; Barbara J. Holler, both of Rochester, Minn.; Peter A. Vandenbergh, Sarasota, Fla.; Ebenezer R. Vedamuthu; Jeffrey K. Kondo, both of Rochester, Minn.

[73] Assignee: Quest International Flavors & Food Ingredients Company, division of Indopco, Inc., Bridgewater, N.J.

[21] Appl. No.: 565,907

[22] Filed: Dec. 1, 1995

[51] Int. Cl.$^6$ ............................ C12N 15/63; C12N 1/21; C07H 21/04

[52] U.S. Cl. ...................... 435/172.1; 435/320.1; 435/252.3; 435/252.32; 435/252.33; 536/23.7

[58] Field of Search ................... 536/23.7; 435/172.3, 435/172.1, 320.1, 252.3, 252.32, 252.33

[56] References Cited

PUBLICATIONS

Jarvis, A.W., et al., Intervirology 32:2–9 (1991).
Hill, C., FEMS Microbiol. Rev. 12:87–108 (1993).
Sing, W.D., et al., J. Dairy Sci. 73:2239–2251 (1990).
McLandsborough, L.A., et al., Appl. Environ. Microbiol. 61:2023–2026 (1995).
Molineaux, I.J., New Biol. 3:230–236 (1991).
Snyder, L., Mol. Microbiol. 15:415–420 (1995).
Hill, C., et al., Appl. Environ. Microbiol. 56:2255–2258 (1990).
Cluzel, P. J., et al., Appl. Environ. Microbiol. 57:3547–3551 (1991).
Durmaz, E., et al., J. Bacteriol. 174:7463–7469 (1992).
Anba, J., et al., J. Bacteriol. 177:3818–3823 (1995).
Hill, C., et al., Appl. Environ. Microbiol. 57:283–288 (1991).
Moineau, S., et al., Appl. Environ. Microbiol. 59:208–212 (1993).
Bidnenko, E., et al., J. Bacteriol. 177:3824–3829 (1995).
Sanders, M. E., et al., Appl. Environ. Microbiol. 52:1001–1007 (1986).
Alatossava, T., et al., Appl. Environ. Microbiol. 57:1346–1353 (1991).
Moineau, S., et al., Appl. Environ. Microbiol. 59:197–202 (1993).
Moineau, S., et al., Appl. Environ. Microbiol. 61:2193–2202 (1995).
Moineau, S., et al., Can. J. Microbiol. 38:875–882 (1992).
Moineau, S., et al., Appl. Environ. Microbiol. 60:1832–1841 (1994).
Jarvis, A.W., Appl. Environ. Microbiol. 36:785–789 (1978).
Sanders, M. E., et al., Appl. Environ. Microbiol. 40:500–506 (1980).
Behnke, D., et al., Virology, 85:118–128 (1978).
Moineau, S., et al., Appl. Environ. Microbiol. 59:2034–2040 (1993).
O'Sullivan, D.J., et al., Appl. Environ. Microbiol. 59:2730–2733 (1993).
Gonzalez, C.F., et al., Appl. Environ. Microbiol. 46:81–89 (1983).

(List continued on next page.)

*Primary Examiner*—Charles L. Patterson, Jr.
*Assistant Examiner*—Kawai Lau
*Attorney, Agent, or Firm*—Ian C. McLeod

[57] ABSTRACT

DNA encoding phage resistance protein which aborts infection by the phage, designated as AbiE. The DNA which is contained in a *Lactococcus lactis* deposited as NRRL-B-21443 and described in SEQ ID NO: 1, is incorporated into a bacterium to encode the AbiE and provide phage resistance. Lactococcus and other bacteria encoding the AbiE are useful in industrial fermentations wherein phage are a problem.

35 Claims, 8 Drawing Sheets

OTHER PUBLICATIONS

Holo, H., et al., Appl. Environ. Microbiol. 55:3119–3123 (1989).

Dinsmore, P.K., et al., Appl. Environ. Microbiol. 60:1129–1136 (1994).

DeVos, W. M., FEMS Microbiol. Rev. 46:281–295 (1987).

Sing, W.D., et al., Appl. Environ. Microbiol. 59:365–372 (1993).

Casey, J., et al., Appl. Environ. Microbiol. 58:3283–3291 (1992).

Durmaz, E., et al., Appl. Environ. Microbiol. 61:1266–1273 (1995).

O'Sullivan, D. J., et al., J. Bacteriol. 177:134–143 (1995).

Terzaghi, G. E., et al., Appl. Environ. Microbiol. 29:807–813 (1975).

Garvey, P. et al. "Cloning and DNA sequence analysis of two abortive infection phage resistance determinants from the Lactococcal plasmid pNP40" Applied and Environmental Microbiology (Dec. 1995), vol. 61, No. 12, pp. 4321–4328.

```
        EcoRI
   1    GAATTCATGTTTTGTTGGATGAGCCATGCATGATAAAGCATTAAATCTTGTTGGACAGGTTTTAAATATA
  71    ACGTATTTCCCTACCTGTTTTGATCATGAATAAATGCAGTTTGTTGTTTGACTGTTCCATCAAGATTAAA
 141    GACATCTGTTTTTTAATTTCATGACGTCACTCACGTAGCAAGGTCGCTTCCCAACTTGGAAAATT
 211    GTATAGTTACGACGACCAGCACGAAAACTATCAAGTAGTGTATCCTGCACCATTTTAAGATATTTGAAT
 281    CTTTAATCGGTAAAACAAGTTGTGCACCATGATATAATGCTCCTTAAATCAATTAATTGCTTTATG
 351    ATAGCAAATACGCTATCATAATAGTATGGAAAATTTGAGTTTGATTATTACGATTGGGCTGAATTGAA
 421    CAGTTCTTAGATCAGTTACCTGATAAAGATGCTGCTAAGTTAATTGCAACCATTCAAAATATTGAAAATA
 491    ATGGCCTCTTAGTCGCTGAAAGACAATTATGGGTCAAAAAACTAGAAAATAATCTTTATGAAATTCGTTC
 561    TAAGCGAGCTTCAAACATCCAAAGAGCGATTTATTTTAAAGTCAAAGGTAGTCAATACATTATTACTAAT
 631    GCGTTCACGAAAAAAAACGCAAAAACCAATGAGTAAACTTGATGCATATGTTGCTGAACGTAGTAAAAATCCC
 701    ATTTGAATAAGGAGGAAAACCAATGAGTAAACTTGATGCATATGTTGCTGAACGTAGTAAAAATCCC
 771    AAATTTCACAATTGTTGAGCAAGAAATAATTTAGCTACTCTGATTGGTAAGTCCATGACCTGCGTG
 841    AAAATATGGGGTTAAGTCAACGTGAATTGCTACTCTGATTGGTAACCACATCAACCATCGCACGCAT
 911    TGAAATGTTCGATGAATGCTTCAACAAAATGTTATCAGAGATTGCCAAGCTACTAATCAACGATTA
 981    ACTATTCAATTAATTCTACATTTTAAGATCTATTATATCATTTAACAAAAATAGCCCTAATAAACC
1051    AAAGTAATTATTAGGGCTATTTATTAGACATGAGTTTTTAAGGGGTTATTTCTAATTATAGTCCCTTAATT
1121    TCCATTTCGTGTCTAATTATTGACATTAGTGACTCCATACAGTAGTACTCTAAGATTTAAGGATAACATCA
1191    ACTTTCAACATAAGCACAATAACTATTTTTTATTATAATTGAAAAGAGAATTGAATTATTACCTATAAA
1261    ACTTAAAGGAGTATAATTATGAAAAAAGAGTTTACTGAATTATATGATTTTATATTGATCCTATTTTC
                  M  K  K  E  F  T  E  L  Y  D  F  I  F  D  P  I  F  L
1331    TTGTAAGATACGGCTATTATGATAGATCTATTAAAACCAAAAAATGAATCCTCCAAAAGTTGAATTAGA
           V  R  Y  G  Y  Y  D  R  S  I  K  T  K  K  M  N  P  P  K  V  E  L  D
1401    CAATGAATATGGAAAATCAGATTCTTTTATTTTAAGTATTTAATATGGAATCCTTGCAGATTATTA
          N  E  Y  G  K  S  D  S  F  Y  F  K  V  F  N  M  E  S  F  A  D  Y  L
```

FIG. 4A

```
1471  AGGAGTCATGATTAAAACACATTTAACGGTAAAAAACCTCTATCAACAGACCCAGTATATTTAATA
        R  S  H  D  L  K  T  H  F  N  G  K  K  P  L  S  T  D  P  V  Y  F  N  I

1541  TTCCAAAAATATAGAAGCTAGAAGACAATATAAGATGCCCAATTTATACAGTTATATGGCATTAAATTA
        P  K  N  I  E  A  R  R  Q  Y  K  M  P  N  L  Y  S  Y  M  A  L  N  Y

1611  TTATATATGTGACAATAAAAAAGAGTTTATAGAAGTATTATTGATAACAAATTTCAACGTCAAAATTT
        Y  I  C  D  N  K  K  E  F  I  E  V  F  I  D  N  K  F  S  T  S  K  F

1681  TTTAATCAATTGAATTTGATTATCCTAAGACACAAGAAATTACACACAAACATTATTATATGGAGGAATAA
        F  N  Q  L  N  F  D  Y  P  K  T  Q  E  I  T  Q  T  L  L  Y  G  G  I  K
                                                                    NcoI
1751  AGAAATTACATTTAGATTATCTAATTTTTATCATACTTTATATACACATAGTATACCATGGATGATTGA
        K  L  H  L  D  L  S  N  F  Y  H  T  L  Y  T  H  S  I  P  W  M  I  D

1821  TGGAAAATCTGCATCTAAACAAAATAGAAAAAAAGGGTTTCTAATACATTAGATACTTTGATTACAGCT
        G  K  S  A  S  K  Q  N  R  K  K  G  F  S  N  T  L  D  T  L  I  T  A

1891  TGTCAATACGACGAAACACATGGCATTCCAACTGGAAATCTATTGTCTAGGATTATTACCGAACTATATA
        C  Q  Y  D  E  T  H  G  I  P  T  G  N  L  L  S  R  I  I  T  E  L  Y  M

1961  TGTGCCATTTGATAAACAAATGGAATATAAGAAGTTTGTGTATTCAAGATATGTAGATGATTTATATT
        C  H  F  D  K  Q  M  E  Y  K  K  F  V  Y  S  R  Y  V  D  D  F  I  F

2031  TCCGTTTACTTTTGAGAATGAAAAGCAAGAATTTTAAATGAATTAATCTAATCTGTCGAGAAAATAAC
        P  F  T  F  E  N  E  K  Q  E  F  L  N  E  F  N  L  I  C  R  E  N  N

2101  TTAATTATTAATGATAATAAAACGAAAGTTGACAATTTCCCGTTTGTTGATAAATCGAGTAAATCGGATA
        L  I  I  N  D  N  K  T  K  V  D  N  F  P  F  V  D  K  S  S  K  S  D  I

2171  TTTTTCTTTTTTGAAAATATTACTTCAACTAATTCCAACGACAAGTGGATTAAAGAAATAAGCAATTT
        F  S  F  F  E  N  I  T  S  N  S  N  D  K  W  I  K  E  I  S  N  F
```

FIG. 4B

```
2241  TATAGATTATTGTGTGAATGAAGAACATTTAGGGAATAAGGGAGCTATAAAATGTATTTCCCAGTTATA
       I  D  Y  C  V  N  E  E  H  L  G  N  K  G  A  I  K  C  I  F  P  V  I

2311  ACAAATACATTGAAACAAAAAAGTAGATACTAAAAATATAGACAATATCTTTTCGAAAGAAACATGG
       T  N  T  L  K  Q  K  K  V  D  T  K  N  I  D  N  I  F  S  K  R  N  M  V

2381  TTACCAATTTTAATGTTTTCGAAAAAATATTAGATTTATCATTAAAAGATTCAAGATTAACTAATAAGTT
       T  N  F  N  V  F  E  K  I  L  D  L  S  L  K  D  S  R  L  T  N  K  F

2451  TTTGACTTTCTTTGAAAATATTAATGAATTTGGATTTTCAAGTTTATCAGTTTCAAATATTGTAAAAAAA
       L  T  F  F  E  N  I  N  E  F  G  F  S  S  L  S  A  S  N  I  V  K  K

2521  TATTTTAGTAATAATTCAAAGGGCTAAAAGAAAAATAGACCACTATCGTAAAATAATTTTAATCAAG
       Y  F  S  N  N  S  K  G  L  K  E  K  I  D  H  Y  R  K  N  N  F  N  Q  E

2591  AATTATATCAAATATTGTGTATATGGTTGTCTTTGAAATAGATGATTATTAAATCAAGAAGAATTACT
       L  Y  Q  I  L  L  Y  M  V  V  F  E  I  D  D  L  L  N  Q  E  E  L  L

2661  AAACTTAATTGATTTAAAATATTAAATATGGAAATATTCTTAATTTGGACGATTTTATCCTAAAGAATAGT
       N  L  I  D  L  N  I  D  D  Y  S  L  I  L  G  T  I  L  Y  L  K  N  S

2731  TCATATAAATTGGAAAAATTATTAAAAAAATAGATCAATTATTATTAATACTCATGCCAACTACGACG
       S  Y  K  L  E  K  L  L  K  K  I  D  Q  L  F  I  N  T  H  A  N  Y  D  V

2801  TTAAAACTTCTCGTATGGCAGAGAAATTATGGCTATTTCGTTATTTCGTTTATTTTTATTTTTAAATTGTAAGAA
       K  T  S  R  M  A  E  K  L  W  L  F  R  Y  F  Y  F  F  F  L  N  C  K  N

EcoRV
2871  TATTTTAGTCAAAAGAGATAAAATAGTTATTGTCAATCTCAAAACTATAATTCAGGACAGAACGGATAT
       I  F  S  Q  K  E  I  N  S  Y  C  Q  S  Q  N  Y  N  S  G  Q  N  G  Y

2941  CAAACAGAACTTAATTGGAATTATATTAAAGGTCAAGGAGGATCTTAGAGCCGAATAACTTTTTTAATG
       Q  T  E  L  N  W  N  Y  I  K  G  Q  G  K  D  L  R  A  N  N  F  F  N  E
```

FIG. 4C

```
3011  AATTGATAGTAATAAAGAAGTTTGGTTAATTTCTTGTGGTGAGAACGAAGATTTCAAATATTTAAATTGATA
        L  I  V  K  E  V  W  L  I  S  C  G  E  N  E  D  F  K  Y  L  N  *
3081  AGTATTTGAAATCTATTATTAGTTCCTGAAAAAAATAGCTGTGTCTTGTCAATATAAATGACAAGACACAG
3151  CTATTTTTTAATTTTGAAATTTATAATTTAAATGAACATTTTTGTAAGAAACCTTTTTTCTGTTCT
3221  TTCAATAAATCTAATTCCGCTGATGAAGAGCGATAGTGTCATCTAGCTGTTAAAGAATGAACCTATTT
3291  TTTGTGTGCTCTGAATTATTCTGAGGAATCGATAGCTTCAGTTCAGTCAACATGTCCATAACAATGTACGG
3361  AATATTCCCTGTACGAGCTTCCTGTTTTATTTTTTTAGGCAGCTTATTCCAATTTCTGAAAATATAAAA
3431  CTTCTATCTACTAGAAACTCTTGGAGCACATAAGTTCGTTGATAGGCATTGAACTTATTATCCGGCTAAA
3501  TGCATGTATCCAACTGTTGCTCCATTACCTGCAATTGTAATGACGGTCCTTCAAACGCTGCTACATCGA
3571  TCCTATATATTTTTAATTCCAGAAGTATAAAAATCATACTTGCCATTTCAACCATTGCATTGCATCTAA
3641  TTTTCCGGTGCTTATTTTAGTAATATCTCCTAACTTACGCTCTTCCCAATCGTCAGCAAACCCGCAAAT
3711  CGCAAATTCAGGAACTTTAGCCCCATTTTTGTAAGAAACATTTTTGTAAGAAGCCTTTTTTCTGTTCCTTGA
3781  GCAAATCTAACTTACGCTGCAGGGACACTTATTATAGCTTCTTAATATCAGTAGAATTAATACTTTCAGCTGTTATCCAGCTGCTTGAAGAATGAACCGATTTGTC
3851  TTGTTCCCTCAATTGCAGGGACACTTAGTCCAATACCCGTCGGACTTCATTTTACCAAGATTTGAAATATAAATTCAT
3921  GATCCAGTGCTATATCTAGTCCAATACCCGTCGGACTTCATTTTACCAAGATTTGAAATATAAATTCAT
3991  TACCTTTATGGCAGCAACATCCGACCAATAACAAGTCATAAGCTGTTTTACCAACATATCTCCAACCGG
4061  TGCTCGGACACTTAGAATGAGAGATCATCTTTTCAGCTGTTTAGTAACTTGAGTGTCCATACTCTCGGT
4131  AAAACACGACCATTTCATGTCAGCATTCAGCATTACCTTGCACACAAGAATATAATCATTAGGATCATCAGTATAAT
4201  TTTCTGAATTAGGAGACTGTCCCATCACTATCGAACTTCGAACTTACGCCAGTTCCCATTCATC
4271  CGTGAATCCTTTAAATCGCAATTCTGGAACTTTCTTTTTAACTGAATCATCTATTTTCGCCATAGTCCCC
4341  ACCATTTTTCTTGGTTTTTCTTGTTCTTCTATCCTTTTTTTGATCTTTGATTGTTCTTAAGTGTTGAATTC
                                                                    EcoRI
4411  CTTCTCTTTAAGAGCGTTCACTTCATCTTTATATTGATTGTCTAAGTGTTTGAATTC
```

FIG. 4D

DNA ENCODOING PHAGE ABORTIVE INFECTION PROTEIN FROM LACTOCOCCUS LACTIS AND METHOD OF USE THEREOF

BACKGROUND OF THE INVENTION (1) Field of the Invention

The present invention relates to DNA isolated in a plasmid or in a bacterium encoding a phage resistance protein (designated as AbiE) which aborts infection of the bacterium by the phage. In particular the present invention relates to methods of using the DNA to provide the phage resistance.

(2) Description of Related Art

Lactococcus lactis is widely used in mesophilic milk fermentations to produce cheese, buttermilk, cottage cheese and sour cream. Due to the expanding activities in these industries, there is pressure on L. lactis starter cultures to perform at industrial standards of consistency and efficiency. Phages are the leading cause of fermentation failures during the manufacture of these cultured dairy products (Jarvis A. W., et al., Intervirology 32:2–9 (1991)). They can ruin a fermentation by inactivating the inoculated, sensitive cultures. Since identification of the causal agent in the mid-30s, the dairy industry has learned to manage with this natural phenomenon by developing various solutions such as better sanitation, process modifications and use of phage-resistant cultures (Hill, C., FEMS Microbiol. Rev. 12:87–108 (1993)).

Extensive studies have been carried out on the innate phage resistance mechanisms of L. lactis strains (for review see Hill, C., FEMS Microbiol. Rev. 12:87–108 (1993)). Native barriers against phages have been found and most of them are encoded on plasmids. More than 40 plasmids encoding a variety of phage resistance mechanisms have been identified (Hill, C., FEMS Microbiol. Rev. 12:87–108 (1993)). These anti-phage systems are currently classified in three groups based on their mode of action: blocking of phage adsorption, restriction/modification (R/M), and abortive infection (Abi).

Amongst the natural L. lactis phage resistance mechanisms, the Abi systems are believed to be the most powerful due to their overall effects (Sing, W. D., et al., J. Dairy Sci. 73:2239–2251 (1990)). In a classical abortive infection, the phage lytic cycle is inhibited but after adsorption, DNA injection and early phage gene expression. The end result is the typical Abi+ phenotype of reduced burst size and plaque size (McLandsborough, L. A., et al., Appl. Environ. Microbiol. 61:2023–2026 (1995); Molineux, I. J., New Biol. 3:230–236 (1991); Sing, W. D., et al., J. Dairy Sci. 73:2239–2251 (1990); Snyder, L., Mol. Microbiol. 15:415–420 (1995)). Generally, the host is also killed in the abortive process. This suicidal outcome traps the phages within the infected cell and limits their dissemination (Sing, W. D., et al., J. Dairy Sci. 73:2239–2251 (1990)).

Many Abi systems have been identified in other bacterial genera (for review see Molineux, I. J., New Biol. 3:230–236 (1991); and Snyder, L., Mol. Microbiol. 15:415–420 (1995)). Some of these systems have been studied extensively but the molecular basis remains somewhat unclear (Snyder, L., Mol. Microbiol. 15:415–420 (1995)). Recent evidence are now only leading to more specific models for their action (Molineux, I. J., New Biol. 3:230–236 (1991); and Snyder, L., Mol. Microbiol. 15:415–420 (1995)). Likewise, Abi systems are very poorly understood in L. lactis (Sing, W. D., et al., J. Dairy Sci. 73:2239–2251 (1990)). To date, five Abi systems have been characterized to molecular level; AbiA (Hill, C., et al., Appl. Environ. Microbiol. 56:2255–2258 (1990), AbiB (Cluzel, P. J., et al., Appl. Environ. Microbiol. 57:3547–3551 (1991), AbiC (Durmaz, E., et al., J. Bacteriol. 174:7463–7469 (1992), AbiD (McLandsborough, L. A., et al., Appl. Environ. Microbiol. 61:2023–2026 (1995) and AbiD1 (Anba, J., et al., J. Bacteriol. 177:3818–3823 (1995). These systems were isolated from different L. lactis strains. There is no homology between the Abi proteins except for AbiD and AbiD1 which shared 28% identity (52% similarity). This was the first indication on the existence of a possible family of Abi proteins in L. lactis (Anba, J., et al., J. Bacteriol. 177:3818–3823). The absence of homology between the other L. lactis Abi mechanisms suggests different mode of action and/or phage targets. Very limited information is available on the molecular mechanisms of L. lactis Abi systems. AbiA is believed to somehow interfere with DNA replication of small isometric phages (Hill, C., et al., Appl. Environ. Microbiol. 57:283–288 (1991); and Moineau, S., et al., Appl. Environ. Microbiol. 59:208–212 (1993)). AbiC does not prevent phage DNA replication but reduces the synthesis of structural phage proteins in infected cells (Durmaz, E., et al., J. Bacteriol. 174:7463–7469 (1992); and Moineau, S., et al., Appl. Environ. Microbiol. 59:208–212 (1993)). Recently, Bidnenko et al. (Bidnenko, E., et al., J. Bacteriol. 177:3824–3829 (1995)) reported that AbiD1 interacted with a small isometric phage operon which contained 4 open reading frames (ORFS). It was proposed that AbiD1 and the orf1 gene product interacted to prevent translation of orf3 RNA (Bidnenko, E., et al., J. Bacteriol. 177:3824–3829 (1995)).

Industrial L. lactis strains with enhanced phage resistance have been constructed by introducing natural plasmids containing Abi systems into phage-sensitive strains (Sanders, M. E., et al., Appl. Environ. Microbiol. 52:1001–1007 (1986)). These improved strains have already been successfully employed for large scale dairy fermentations. However new phages capable of overcoming the introduced Abi defense system have emerged (Alatossava, T., et al., Appl. Environ. Microbiol. 57:1346–1353 (1991); and Moineau, S., et al., Appl. Environ. Microbiol. 59:197–202 (1993)). Thus, the search for novel phage resistance mechanisms is an ongoing objective for culture suppliers (Moineau, S., et al., Appl. Environ. Microbiol. 61:2193–2202 (1995)).

Lactococcal phages are classified in 12 different species based on morphology and DNA homology (Jarvis, A. W., et al., Intervirology 32:2–9 (1991)). Only three have been studied for genetic details because they are commonly encountered worldwide in dairy plants (Jarvis, A. W., et al., Intervirology 32:2–9 (1991)). Members of the species 936 (small isometric heads), c2 (prolate heads) and P335 (small isometric heads) have been, by far, the most disturbing lactococcal phages (Jarvis, A. W., et al., Intervirology 32:2–9 (1991); and Moineau, S., et al., Can. J. Microbiol. 38:875–882 (1992)). DNA—DNA hybridization studies have revealed the absence of significant DNA homology between the three species (Jarvis, A. W., et al., Intervirology 32:2–9 (1991)). The current consensus is that the 936, P335 and c2 species are genetically distinct and L. lactis starter cultures should be resistant against these phages (Moineau, S., et al., Appl. Environ. Microbiol. 61:2193–2202 (1995)).

OBJECTS

It is an object of the present invention to provide DNA encoding a sixth and novel abortive infection mechanism (Abi) from L. lactis which acts prior to or at the phage DNA replication and shares no homology with the previously isolated Abi from *L. lactis*. Further, it is an object of the present invention to provide a novel Abi system which is efficient against 936, c2 and P335 phages.

Further, it is an object of the present invention to provide a method and bacteria which prevent phage inactivation of *Lactococcus lactis* strains. Further still, it is an object of the present invention to provide recombinant bacteria which are economical to prepare and effective in phage inhibition. These and other objects will become increasingly apparent by reference to the following description and the drawings.

BRIEF DESCRIPTION OF DRAWINGS

FIGS. 4A to 4D are a nucleotide sequence of the 4.5-kb EcoRI fragment from pSRQ800 as shown in SEQ ID NO:1. The deduced amino acid sequence of the only significant open reading frame is presented. The putative promoter and RBS are underlined.

DESCRIPTION OF PREFERRED EMBODIMENTS

Figure 1:
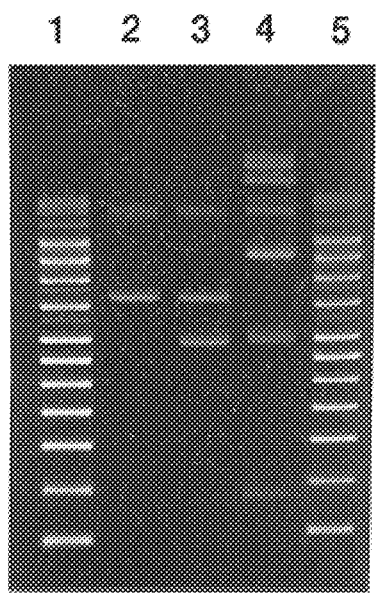
FIG. 1 is a photograph of an electrophoresis gel showing a plasmid analysis of *Lactococcus lactis* strains. Lanes: 1 and 5, supercoiled DNA ladder (Gibco/BRL, Grand Island, N.Y.); 2, *L. lactis* SMQ-16; 3, *L. lactis* SMQ-20; 4, *L. lactis* W-1 (containing plasmid pSRQ800).

The present invention relates to an isolated DNA encoding a protein designated as AbiE which in a *Lactococcus lactis* increases resistance to phages by aborting infection of *Lactococcus lactis* by phages, particularly as contained in *Lactococcus lactis* SMQ20 deposited as NRRL-B-21443 and as set forth in SEQ ID NO:1.

The present invention also relates to a recombinant plasmid containing DNA encoding a protein designated as AbiE which in a *Lactococcus lactis* increases resistance to phages by aborting infection of *Lactococcus lactis* by phages, particularly containing the DNA set forth previously.

The present invention also relates to a bacterium harboring a recombinant plasmid containing DNA encoding a protein designated as AbiE which in a *Lactococcus lactis* increases resistance to phages by aborting infection of *Lactococcus lactis* by phages, particularly a bacterium harboring DNA as set forth previously. The bacterium are preferably Lactococcus, Lactobacillus, Leuconostocs, Pediococcus, Streptococcus thermophilus, Enterococcus, and Bifidobacterium.

The present invention further relates to a method of imparting phage resistance to a bacterium which is phage sensitive which comprises transferring DNA encoding a protein designated as AbiE which increases resistance to phages by aborting infection of *Lactococcus lactis* by phages into the bacterium to impart the phage resistance. Further the present invention relates to a method for fermenting a dairy product, the improvement which comprises using a culture of *Lactococcus lactis* for the fermenting containing transferred DNA encoding a protein designated as AbiE which increases resistance to phages by aborting infection of *Lactococcus lactis* by phages to impart the phage resistance and to produce the dairy product.

Most particularly the present invention relates to *Lactococcus lactis* naturally lacking in phage resistance and containing transferred DNA encoding a protein designated as AbiE which increases resistance to phages by aborting infection of *Lactococcus lactis* by phages, wherein the DNA has a sequence essentially as set forth in SEQ ID NO:1 to impart phage resistance to the *Lactococcus lactis*.

The natural plasmid pSRQ800 was isolated from *Lactococcus lactis* subsp. lactis W1. When introduced into a phage-sensitive *L. lactis* strain, pSRQ800 conferred strong phage resistance against small isometric phages of the 936 and P335 species. It had very limited effect on prolate phages of the c2 species. The phage resistance mechanism encoded on PSRQ800 is a temperature-sensitive abortive infection mechanism (Abi). Plasmid pSRQ800 was mapped and the Abi genetic determinant localized. Cloning and sequencing of the Abi system allowed the identification of a single open reading frame. This ORF coded for a predicted protein of 599 amino acids with an estimated molecular weight of 71.4 kDa and a pI of 8.0. No significant DNA or protein homology was observed with databases. This novel phage resistance mechanism was named AbiE. No phage replication or production of phage major capsid proteins were detected in infected AbiE+ *L. lactis* cells. This system is believed to act at or prior to phage DNA replication. When cloned into a high copy vector, AbiE became effective against the c2 species. Thus when delivered in an appropriate vector, AbiE system was efficient against the three most commonly found lactococcal phage species.

The plasmid pSRQ800 is contained in a deposit of *Lactococcus lactis* SMQ-20 deposited under the Budapest Treaty with the Northern Regional Research Laboratory in Peoria, Ill. on May 17, 1995 as NRRL-B-21443. DNA plasmid pSRQ700 encoding a restriction or modification system (LlaDCHI) is deposited under the Budapest Treaty as NRRL-B-21337 on Sep. 29, 1994 and is used with pSRQ800 to produce a synergistic result. This DNA is described in U.S. application Ser. No. 08/366,480, filed Dec. 30, 1994, which is incorporated by reference herein. The DNA sequence is deposited with GenBank (V16027).

EXAMPLE 1

Materials and Methods

Bacterial strains, plasmids, and media. Strains and plasmids used in this application are listed in Tables 1 and 2.

*Escherichia coli* was grown at 37° C. in LB broth. *Lactococcus lactis* strains were grown at 30° C. in M17 (Terzaghi, B. E., et al., Appl. Environ. Microbiol. 29:807–813 (1975)) supplemented with 0.5% glucose (GM17) or 0.5% lactose (LM17). When appropriate, antibiotics were added as follows: for *E. coli*, 50 µg of ampicillin per ml, 10 µg of tetracycline per ml, and 20 µg of chloramphenicol per ml; for *L. lactis*, 5 µg of chloramphenicol per ml, and 5 µg of erythromycin per ml. Bacteriophage propagation and assays. Bacteriophages used in this study are listed in Table 1.

TABLE 1

Bacterial Strains and Bacteriophages used.

| Bacterial strains or and phages | Relevant characteristics[a] | Source[b] |
|---|---|---|
| *Lactococcus lactis* | | |
| LM0230 | Plasmid free, host for 936 and c2 phages; Lac[-] | |
| UL8 | Multiple plasmids, host for P335 phages; Lac[+] | |
| W1 | Multiple plasmids including pSRQ800; Lac[+] | This invention |
| SMQ-16 | LM0230 (pSA3); Lac[-] Em[r] | |
| SMQ-20 | LM0230 (pSA3, pSRQ800); Lac[-] Em[r] Abi[+] | This invention |
| SMQ-37 | LM0230 (pSRQ801); Lac[-] Em[r] | This invention |
| SMQ-38 | LM0230 (pSRQ802); Lac[-] Em[r] Abi[+] | This invention |
| SMQ-39 | LM0230 (pSRQ701); Lac[-] Em[r] R[+]/M[+] | |
| SMQ-52 | LM0230 (pSRQ804); Lac[-] Em[r] | This invention |
| SMQ-54 | LM0230 (pSRQ806); Lac[-] Em[r] | This invention |
| SMQ-57 | LM0230 (pSRQ809); Lac[-] Em[r] | This invention |
| SMQ-86 | UL8 (pSA3); Lac[+] Em[r] | This invention |
| SMQ-88 | UL8 (pSRQ802); Lac[+] Em[r] Abi[+] | This invention |
| SMQ-130 | LM0230 (pSRQ813); Lac[-] Cm[r] Abi[+] | This invention |
| SMQ-138 | LM0230 (pSRQ701, pSRQ813); Lac[-] Em[r] Cm[r] R[+]/M[+] Abi[+] | This invention |
| SMQ-143 | LM0230 (pSRQ815); Lac[-] Cm[r] Abi[+] | This invention |
| SMQ-251 | LM0230 (pMIG3); Lac[-] Cm[r] | This invention |
| SMQ-252 | LM0230 (pNZ123); Lac[-] Cm[r] | This invention |
| *Escherichia coli* | | |
| DH5α | Transformation host | Gibco/BRL |
| SMQ-92 | DH5α (pSRQ810); Ap[r] | This invention |
| SMQ-116 | DH5α (pSRQ812); Ap[r] | This invention |
| SMQ-129 | DH5α (pSRQ814); Ap[r] | This invention |
| Bacteriophages | | |
| φp2 | Small isometric headed, 936 species, 30.5 kb | L.L. McKay |
| φsk1 | Small isometric headed, 936 species, 28.1 kb | L.L. McKay |
| φjj50 | Small isometric headed, 936 species, 30.5 kb | |
| φc2 | Prolate headed, c2 species, 20.7 kb | |
| φm13 | Prolate headed, c2 species, 20.2 kb | W.E. Sandine |
| φeb1 | Prolate headed, c2 species, 19.6 kb | L.L. McKay |
| φu136 | Small isometric headed, P335 species, 28.8 kb | |
| φQ30 | Small isometric headed, P335 species, 37.0 kb | |
| φQ33 | Small isometric headed, P335 species, 29.6 kb | |

Table 1, Footnotes
[a]Abi[+], active abortive infection mechanism; Ap[r], ampicillin resistance; Cm[r], chloramphenicol resistance; Em[r], erythromycin resistance; Lac, lactose-fermenting ability; R[+]/M[+], active restriction/modification enzymes;
[b]L.L. McKay, University of Minnesota, Minneapolis; W.E. Sandine, Oregon State University, Corvallis;

TABLE 2

Plasmids used in this invention.

| Plasmid | Relevant characteristics | Source |
|---|---|---|
| pBS | Cloning vector for sequencing, Ap[r], 2.9-kb | Stratagene |
| pMIG3 | Shuttle vector, Cm[r], 5.5-kb | |
| pNZ123 | Shuttle vector, Cm[r], 2.5-kb | |
| pSA3 | Shuttle vector, Cm[r] Tc[r] Em[r], 10.2-kb | |
| pSR701 | 7.0-kb EcoRI fragment from pSRQ700 cloned into pSA3; Cm[s] Tc[r] Em[r] R[+]/M[+] | |
| pSRQ800 | Resident plasmid of W1, Abi[+], 8.0-kb | This invention |
| pSRQ801 | 3.5-kb EcoRI fragment from pSRQ800 cloned into pSA3; Cm[s] Tc[r] Em[r] | This invention |
| pSRQ802 | 4.5-kb EcoRI fragment from pSRQ800 cloned into pSA3; Cm[s] Tc[r] Em[r] | This invention |

TABLE 2-continued

Plasmids used in this invention.

| Plasmid | Relevant characteristics | Source |
| --- | --- | --- |
| pSRQ804 | 5.7-kb NcoI fragment from pSRQ800 cloned into pSA3; $Cm^s$ $Tc^r$ $Em^r$ | This invention |
| pSRQ806 | 1.8-kb NcoI-EcoRI fragment from pSRQ800 cloned into pSA3; $Cm^s$ $Tc^r$ $Em^r$ | This invention |
| pSRQ809 | 8.0-kb EcoRV fragment from pSRQ800 cloned into pSA3; $Cm^r$ $Tc^s$ $Em^r$ | This invention |
| pSRQ810 | 1.5-kb EcoRV-EcoRI from pSRQ800 cloned into pBS; $Ap^r$ | This invention |
| pSRQ812 | 1.2-kb EcoRV-ScaI from pSRQ802 cloned into pBS; $Ap^r$ | This invention |
| pSRQ813 | 4.5-kb fragment from pSRQ800 cloned into pMIG3; $Cm^r$ | This invention |
| pSRQ814 | 1.8-kb EcoRI-ScaI from pSRQ802 cloned into pBS; $Ap^r$ | This invention |
| pSRQ815 | 4.5-kb EcoRI fragment from pSRQ802 cloned into pNZ123; $Cm^r$ | This invention |

$Abi^+$, active abortive infection mechanism; $Ap^r$, ampicillin resistance; $Cm^r$, chloramphenicol resistance; $Cm^s$, sensitive to chloramphenicol; $Em^r$, erythromycin resistance; $Tc^r$, tetracycline resistance; $Tc^s$, sensitive to tetracycline; $R^+/M^+$, active restriction/modification enzymes.

Bacteriophages c2, p2, sk1, and jj50 were a gift from T. R. Klaenhammer (North Carolina State University). All phages were isolated from a single plaque with a 1-ml sterile pipette (Moineau, S., et al., Appl. Environ. Microbiol. 60:1832–1841 (1994)). They were transferred to GM17 containing 10 mM $CaCl_2$ previously inoculated (1%) with an overnight culture of the host strain. They were incubated at 30° C. until lysis and filtered through a 0.45 µm filter (Acrodics, Gelman Sciences, Ann Arbor, Mich.). High phage titers were then obtained by the method of Jarvis (Jarvis, A. W., Appl. Environ. Microbiol. 36:785–789 (1978)). Efficiency of plaquing (EOP) and adsorption assays were performed as described by Sanders and Klaenhammer (Sanders, M. E., et al., Appl. Environ. Microbiol. 40:500–506 (1980)). Cell survival was assayed by the method of Behnke and Malke (Behnke, D., et al., Virology, 85:118–128 (1978)) using a MOI of 3. One-step growth curves, center of infection (COI) assays, burst size and latent period determination were performed as described previously (Moineau, S., et al., Appl. Environ. Microbiol. 59:208–212 (1993)). The efficiency at which COI formed (ECOI) was obtained by dividing the number of COI from the resistant strain by the number of COI from the sensitive strain. The intracellular replication of φul36 DNA was also followed at time intervals after phage infection using the Hill et al. procedure (Hill, C., et al., Appl. Environ. Microbiol. 57:283–288 (1991)). The production of φul36 major capsid protein (MCP) was followed at time intervals after phage infection using monoclonal antibodies and a sandwich enzyme-linked immunosorbent assay (ELISA) as described previously (Moineau, S., et al., Appl. Environ. Microbiol. 59:2034–2040 (1993); and Moineau, S., et al., Appl. Environ. Microbiol. 59:208–212 (1993)).

DNA isolation and manipulation. Plasmid DNA from *E. coli* was isolated as described previously (Moineau, S., et al., Appl. Environ. Microbiol. 60:1832–1841 (1994)). Large quantities of *E. coli* plasmid DNA were isolated with the QIAGEN (Chatsworth, Calif.) plasmid MIDI or MAXI kit. Plasmid DNA from *L. lactis* was isolated using the method of O'Sullivan and Klaenhammer (O'Sullivan, D. J., et al., Appl. Environ. Microbiol. 59:2730–2733 (1993)). Large quantities of lactococcal plasmid DNA were obtained as described by Gonzalez and Kunka (Gonzalez, C. F., et al., Appl. Environ. Microbiol. 46:81–89 (1983)) . Restriction endonucleases (Gibco/BRL, Grand Island, N.Y.) and T4 DNA ligase (Boehringer Mannheim, Indianapolis, Ind.) were used as described by the manufacturer's instructions.

Electroporation. *E. coli* was electroporated as previously described (Moineau, S., et al., Appl. Environ. Microbiol. 60:1832–1841 (1994)). *L. lactis* was grown in GM17 supplemented with 0.5M sucrose and 1% glycine and electroporated according to the Holo and Nes procedure (Holo, H., et al., Appl. Environ. Microbiol. 55:3119–3123 (1989)) as modified previously (Moineau, S., et al., Appl. Environ. Microbiol. 60:1832–1841 (1994)).

Figure 3:
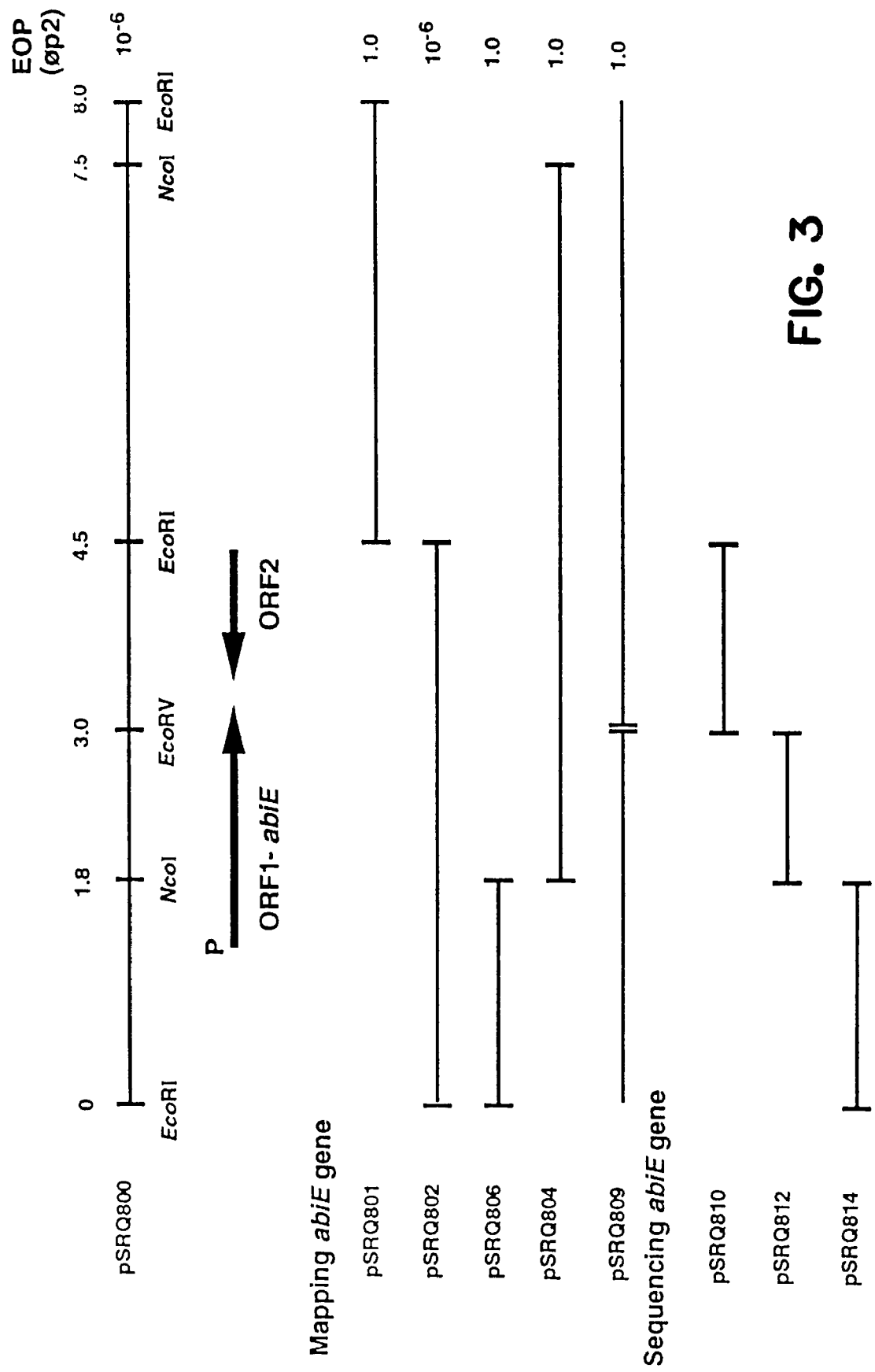
FIG. 3 is a linear restriction map of plasmid pSRQ800 and subclones used to localized the abiE gene. The DNA regions represented by the horizontal lines were subcloned into pSA3. The lines are bordered with vertical bars which indicates the site of cloning. The clones were electroporated in *L. lactis* LM0230 and the transformants tested for resistance against φp2. For sequencing purposes, the 4.5-kb EcoRI fragment was cut in three segments and subcloned into pBS.

Sequencing. The entire abi gene (4.5-kb EcoRI fragment from pSRQ800) could not be cloned in *E. coli* pBluescript KS+. The 4.5-kb insert was segmented into 3 small fragments (FIG. 3), subcloned into pBS and transformed into *E. coli* DH5α with blue and white color selection using IPTG (isopropyl-β-D-thiogalactopyranoside) and X-Gal (5-bromo-4-chloro-3-indoly-β-D-galactopyranoside). The resulting clones were named pSRQ810, pSRQ812 and pSRQ814 (FIG. 3). Nested deletions were made in both orientation from pSRQ810, pSRQ812 and pSRQ814 with an ERASE-A-BASE kit (Promega, Madison, Wis.). Plasmid DNA was extracted from the nested clones with QIAGEN and used directly for sequencing. The sequencing reactions were performed with the DYEDEOXY TERMINATOR TAQ sequencing kit for use on the model 373A automated DNA sequencing system (Applied Biosystems, Foster City, Calif.). The T7 and T3 primers were used for annealing.

DNA and protein analysis. The DNA sequence was analyzed with the Genetics Computer Group (Madison, Wis.) sequence analysis software. The GenBank (release 90, 15 August 95) and SwissProt (release 31.0, March 95) databases were searched for homology with the deduced abiE gene and protein.

Nualeotide sequence accession number. The complete sequence of 4,467 bp was deposited in the GenBank database and is available under the accession number U35629.

Results

Isolation of PSRQ800. The objective of this study was to identify phage resistance mechanism(s) present in *Lactococcus lactis* subsp. lactis W1. The total plasmid DNA of W1 was co-electroporated with the shuttle vector pSA3 into the laboratory strain *L. lactis* LM0230 which is phage-sensitive and plasmid-free. LM0230 was used because of its sensitivity to phages of the 936 and c2 species. The W1/pSA3 DNA ratio used for electroporation was 10:1. Erythromycin-resistant colonies were obtained (due to pSA3) and tested for phage resistance by spot assay ($10^4$ φp2/spot). Some phage-resistant transformants were obtained, analyzed and found to contain pSA3 and a 8.0-kb plasmid which was named pSRQ800 (FIG. 1). One phage-resistant transformant was selected and named *L. lactis* SMQ-20.

Effectiveness of pSRQ800 on three lactococcal phage species.

*L. lactis* SMQ-20 was tested for resistance against three small isometric-headed phages of the 936 species as well as three prolate-headed phages of the c2 species (Table 1). These 6 phages were individually tested on SMQ-20 and their EOPs are presented in Table 3. EOPs ranging from $10^{-6}$ to $10^{-7}$ were obtained for the 936-type phages φp2, φsk1 and φjj50 whereas EOPs of $10^{-1}$ were obtained with prolate φc2, φml3 and φeb1 (Table 3).

TABLE 3

EOPs of lactococcal phages at 30° C. on
Lactococcus lactis strains harboring PSRQ800.

| Phage | EOP |
|---|---|
| 936 species[a] | |
| φp2 | $4.6 \times 10^{-6}$ |
| φsk1 | $7.5 \times 10^{-7}$ |
| φjj50 | $6.0 \times 10^{-6}$ |
| c2 species[a] | |
| φc2 | $2.3 \times 10^{-1}$ |
| φml3 | $3.3 \times 10^{-1}$ |
| φeb1 | $2.7 \times 10^{-1}$ |
| P335 species[b] | |
| φul36 | $3.2 \times 10^{-6}$ |
| φQ30 | $3.0 \times 10^{-5}$ |
| φQ33 | $2.7 \times 10^{-8}$ |

[a]The EOP of the 936 and c2 phages was tested on L. lactis SMQ-20. The EOP of these phages is 1.0 on L. lactis LM0230.
[b]The EOP of the P335 phages was tested on L. lactis SMQ-88. The EOP of these phages is 1.0 on L. lactis SMQ-86.

The activity of pSRQ800 was also tested against P335 phages. Since LM0230 cannot replicate P335 phages, pSRQ800 was introduced into an appropriate host. L. lactis UL8 was electroporated with pSRQ802, a derivative of pSRQ800 (see below), and the transformant named SMQ-88. The EOPs of three P335 phages (φul36, φQ30 and φQ33) on SMQ-88 are presented in Table 3. The EOPs were variable ranging from $10^{-5}$ to $10^{-8}$. These results showed that the phage resistance mechanism encoded on pSRQ800 was effective against small isometric phages of the 936 and P335 species. However, pSRQ800 had very limited effect on prolate phages (c2 species).

Effect of temperature on pSRQ800. The effect of temperature on the activity of pSRQ800 was tested using φp2. Similar EOPs were obtained at 21° C. and at 30° C. However, the EOP of φp2 increased from $4.6 \times 10^{-6}$ to $6.7 \times 10^{-2}$ at 38° C. indicating that the phage resistance mechanism encoded on pSRQ800 is heat-sensitive. Identification of the phage resistance mechanism on pSRQ800.

The type of phage defense mechanism located on PSRQ800 was examined. Adsorption experiments indicated that phages adsorbed to the same level (approximately between 90 to 95%) on the phage-sensitive L. lactis LM0230 and on the phage-resistant L. lactis SMQ-20, ruling out the adsorption blocking mechanism.

To determine if the mechanism was a R/M system, L. lactis SMQ-20 was challenged with high concentration of φp2. Phages capable of overcoming the pSRQ800 defense system and forming plaques on SMQ-20 were isolated. When these phages were tested back on SMQ-20, we observed that some phages were still inhibited by pSRQ800 while others were unaffected. These former phages were still untouched by pSRQ800 even after propagation on the sensitive host LM0230, indicating a permanent modification. These mutants or φp2 derivatives are under investigation. Nevertheless, these results ruled out the presence of host-controlled modifications such as R/M systems.

Based on the current classification of lactococcal phage resistance mechanisms, this system was considered an abortive infection mechanism. Furthermore when challenged with phages, L. lactis SMQ-20 exhibited the typical Abi+ phenotype of reduced plaque size.

Figure 2:
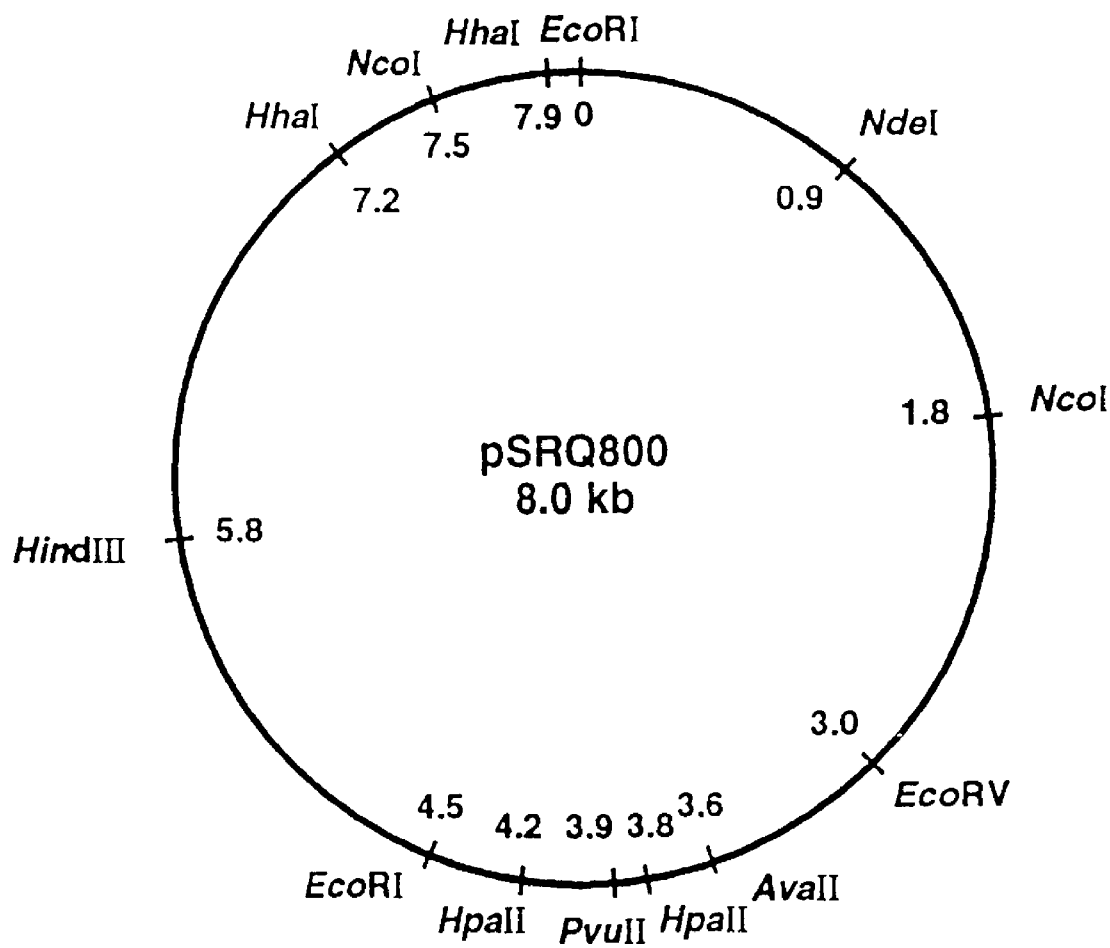
FIG. 2 is a circular restriction map of lactococcal plasmid pSRQ800. Site positions are indicated in kilobases.

Localization of the abi gene on pSRQ800. The plasmid pSRQ800 was mapped using single, double and triple endonuclease digestions. The results are presented in FIG. 2. The following endonucleases did not cut pSRQ800: ApaI, AvaI, BalI, BamHI, HpaI, NruI, PstI, SalI, ScaI, SmaI, SphI, SstI, XbaI, XhoI. Since appropriate restriction sites were present on pSA3 and PSRQ800, total plasmid DNA from L. lactis SMQ-20 was digested with EcoRI, EcoRV and/or NcoI, and religated. The ligation mixture was directly electroporated in E. coli DH5α. After obtaining the appropriate clones, plasmid DNA was electroporated into L. lactis LM0230. The Em[r] transformants were tested for phage resistance. The relevant clones are presented in FIG. 3. Most of the clones (PSRQ801, pSRQ804, pSRQ806, pSRQ809) conferred no resistance (EOP of 1.0) against φp2 (FIG. 3). Only the clone pSRQ802 gave phage resistance similar to pSRQ800 (EOP of $10^{-6}$, FIG. 3). Thus, the full Abi+ phenotype was localized on a 4.5-kb EcoRI fragment.

DNA and protein sequence analysis of the Abi system. The 4.5-kb fragment containing the Abi+ phenotype was sequenced in both directions and found to contain 4,467 bp (FIGS. 4A to 4D). This fragment had a G+C content of 29.5%. Two significant open reading frames (ORFs) were found on the 4.5-kb fragment. The first ORF was localized in one direction from position 1279 to 3075. The second ORF was localized in the other direction from position 4345 to 3491. The clones pSRQ804 and pSRQ809 which contained the full ORF2 but a disrupted ORF1 exhibited no resistance (EOP of 1.0) against φp2 (FIG. 3). We concluded that only ORF1 had all the necessary information to confer the Abi+ phenotype.

The complete abi gene contained 1,797 bp with a very low GC content of 23.9%. A putative ribosome binding site (AAAGGAG) was found 8 bases preceding the abi gene start codon (FIG. 4A to 4D). Putative promoter regions −10 (TATAAT), 16 bp spacer and −35 (AGCACA), were found upstream of the abi gene (FIGS. 4A to 4D). No region of dyad symmetry was found at the end of the abi gene suggesting the presence of a rho-dependent terminator. No significant DNA homology was found between this abi gene and the GenBank database including the previous sequenced L. lactis abi genes. This novel system was named AbiE.

The predicted AbiE protein contained 599 amino acids with an estimated weight of 71,416 Da and a pI of 8.0. No homology to the AbiE protein was found in the SwissProt database, confirming the novelty of AbiE. No transmembrane helix or secretory signals were found indicating that the AbiE protein is most likely intracellular. The Abi+ phenotype was totally abolished with the clone pSRQ809 where the last 42 amino acids were missing from the AbiE protein. This result indicated that the C-terminal of the AbiE protein was critical to the Abi+ phenotype.

Enhancement of AbiE efficiency. The copy number of pSRQ800 was not determined but was estimated to be roughly the same as the low copy vector pSA3 (FIG. 1). The AbiE system was cloned into the high copy plasmid pNZ123 to determine the effect of gene copy number on the AbiE+ phenotype. Previously, it was estimated that pSA3 was present in 5 to 10 copies (Dinsmore, P. K., et al., Appl. Environ. Microbiol. 60:1129–1136 (1994)) whereas pNZ123 was found between 50 to 100 copies in L. lactis (DeVos, W. M., FEMS Microbiol. Rev. 46:281–295 (1987)). The resulting high copy clone and transformant were named pSRQ815 and SMQ-143, respectively. The EOP of φp2 on SMQ-143 was $10^{-8}$ which is 2 negative logs higher than the EOP on SMQ-20 which contained the natural plasmid pSRQ800. Interestingly, the EOP of prolate phage c2 was also significantly decreased on SMQ-143. An EOP of $10^{-4}$ was observed with pSRQ815 whereas EOPs of $10^{-1}$ were observed with pSRQ800 and pSRQ802 (Table 4).

TABLE 4

EOP of φp2 and φc2 on *Lactococcus lactis* strains harboring various phage resistance mechanisms.

| Strains | EOP of φp2 | EOP of φc2 |
|---|---|---|
| LM0230 | 1.0 | 1.0 |
| SMQ-16 (pSA3) | 1.0 | 1.0 |
| SMQ-20 (pSA3 + pSRQ800) | $4.6 \times 10^{-6}$ | $2.3 \times 10^{-1}$ |
| SMQ-38 (pSRQ802) | $2.6 \times 10^{-6}$ | $6.9 \times 10^{-1}$ |
| SMQ-251 (pMIG3) | 1.0 | 1.0 |
| SMQ-130 (pSRQ813) | $1.8 \times 10^{-5}$ | 1.0 |
| SMQ-252 (pNZ123) | 1.0 | 1.0 |
| SMQ-143 (pSRQ815) | $3.8 \times 10^{-8}$ | $1.4 \times 10^{-4}$ |
| SMQ-39 (pSRQ701) | $1.9 \times 10^{-6}$ | $1.7 \times 10^{-4}$ |
| SMQ-138 (pSRQ701 + pSRQ813) | $<10^{-9}$ | $1.1 \times 10^{-4}$ |

These results indicated that multiple copies of abiE gene increase phage resistance against small isometric and prolate phages.

EXAMPLE 2

Another way of increasing the efficiency of Abi system is to supply in trans an another phage resistance mechanism (Sing, W. D., et al., Appl. Environ. Microbiol. 59:365–372 (1993)). Previously, we have isolated a *L. lactis* R/M system named LlaDCHI (formerly LlaII), that was encoded on the plasmid pSRQ700 (Moineau, S., et al., Appl. Environ. Microbiol. 61:2193–2202 (1995)). This plasmid was isolated from the industrial strain *L. lactis* subsp. cremoris DCH-4. The LlaDCHI genes were previously cloned into pSA3 and the Em$^r$ clone named pSRQ701 (Moineau, S., et al., Appl. Environ. Microbiol. 61:2193–2202 (1995)). Phage p2 had an EOP of $10^{-6}$ on *L. lactis* LM0230 harboring pSRQ701 (SMQ-39, Table 4). This phage had also an EOP of $10^{-6}$ on *L. lactis* LM0230 harboring pSRQ800 (SMQ-20, Table 4). The abiE gene was cloned into the vector pMIG3 (which contains a Cm$^r$ gene) and the clone was named pSRQ813. The EOP of φp2 on LM0230 containing pSRQ813 was slightly lower ($10^{-5}$) (SMQ-130, Table 4). Plasmids pSRQ701 and pSRQ813 were electroporated into *L. lactis* LM0230 and the resulting Em$^r$/Cm$^r$ transformant was named SMQ-138. The EOP of φp2 on SMQ-138 was $<10^{-9}$ indicating a full phage resistance phenotype. The EOP of the P335 phage ul136 was also $<10^{-9}$ on another *L. lactis* strain harboring both plasmids (data not shown). These results showed that AbiE and LlaDCHI R/M system, when supplied in trans, can complement each other to enhance phage resistance levels.

Intracellular effects of AbiE system on the phage life cycle. The effects of the AbiE system was tested on the phage ul36 life cycle using the phage-sensitive *L. lactis* SMQ-86 (pSA3) and phage-resistant *L. lactis* SMQ-88 (pSRQ802). Phage ul36 was selected because it was previously used to characterize two other Abi systems, AbiA and AbiC (Moineau, S., et al., Appl. Environ. Microbiol. 59:208–212 (1993)). The replication of φul36 was severely inhibited on SMQ-88 as seen by the EOP of $10^{-6}$ (Table 5 and FIG. 5C). Plaques were reduced in size from 1 mm to pinpoint and difficult to enumerate (data not shown). The average number of surviving cells following phage infection (MOI of 3) was 0.06% on SMQ-86 and 2.65% on SMQ-88 (Table 5).

TABLE 5

Specific effects of AbiE on the lactococcal phage ul36.

| Assays | SMQ-86 | SMQ-88 |
|---|---|---|
| EOP[a] | 1.0 | $3.15 \pm 1.63 \times 10^{-6}$ |
| Cell survival[a] (%) | $5.76 \pm 5.81 \times 10^{-2}$ | $2.65 \pm 0.85$ |
| ECOI[b] | 1.0 | $5.13 \pm 3.57 \times 10^{-3}$ |
| Burst size[a] | $504 \pm 164$ | $36 \pm 27$ |
| Latent period[a] (min) | 75 | 90 |
| DNA replication | +++ | − |
| MCP production[a] (%) | 100 | 1 |

[a]Average of five trials.
[b]Average of ten trials.

AbiE improved cell survival by approximately 50 fold but still a majority of infected cells died.

The ECOI for φul36 on SMQ-88 was 0.0051 indicating that only 5 out of 1000 infected cells successfully release viable phages (Table 5). The burst size of these productive infections was also reduced from an average of 504 phages on the phage-sensitive SMQ-86 to 36 phages on SMQ-88 (Table 5). Furthermore, the phage latent period was longer on SMQ-88 by approximately 15 min. (FIG. 5C). These results indicated that φul36 took more time to complete its life cycle on an AbiE$^+$ host and that the number of released phages was reduced by almost 15 fold. The cumulative effects of AbiE on the cell survival, ECOI, burst size and latent period were responsible for the severely reduced EOP of φul36 on SMQ-88 (Table 5).

Figures 5A, 5B:
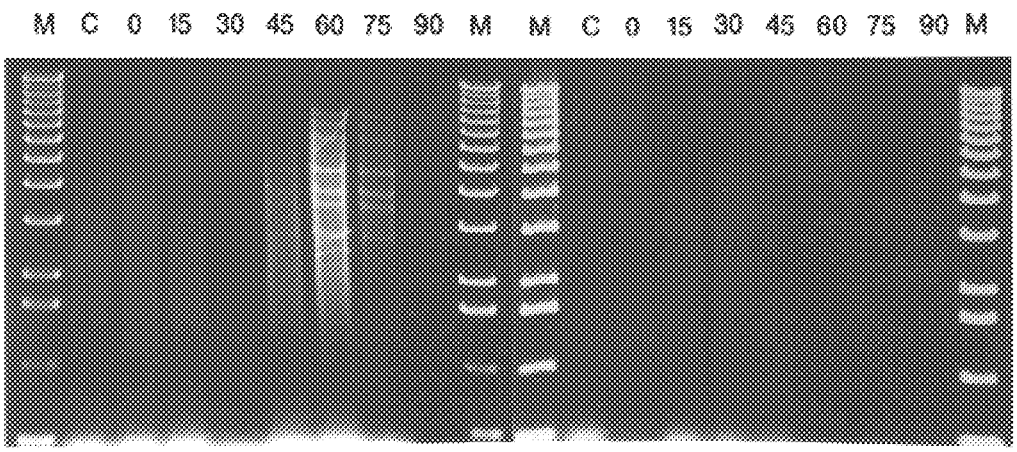
FIGS. 5A and 5B are electrophoresis gels showing φul36 DNA replication followed at time intervals during infection of *L. lactis* SMQ-86 (left side) and SMQ-88 (right side). 1-ml samples were taken at time intervals and the total DNA isolated according to the Hill et al. procedure (Hill, C., et al., Appl. Environ. Microbiol. 57:283–288 (1991)). Total DNA was cut with EcoRV and a sample run on a 0.7% agarose gel. Lane M, 1-kb ladder (Gibco/BRL); Lane C, DNA sample prior to phage infection; Lane 0, 15, 30, 45, 65, 75 and 90 indicates time intervals (min.).
Figure 5C:
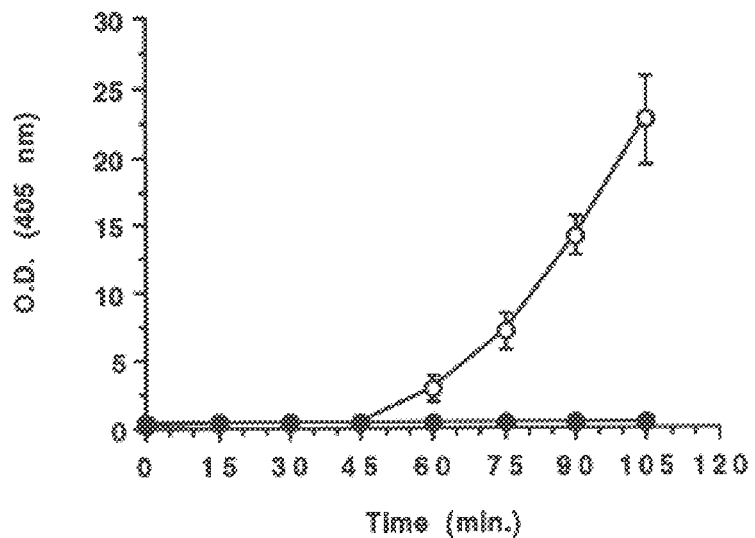
FIG. 5C is a graph showing accumulation of the major capsid protein of φuL36 followed at time intervals during infection of *L. lactis* SMQ-86 and SMQ-88 using an ELISA detection system described previously (Moineau, S., et al., Appl. Environ. Microbiol. 59:208–212 (1993)). An O.D. of 0.389±0.132 was obtained at time 105 with infected SMQ-88 cells. Symbols: ○, SMQ-86 (pSA3); ●, SMQ-88 (pSRQ802). Error bar indicates standard deviation for 5 trials. The background level of non-infected cells was 0.296±0.085. Substantial accumulation of protein was produced in φuL36 infected SMQ-86 cells.

The intracellular replication of φul36 DNA was followed on SMQ-86 and SMQ-88 (FIG. 5A and 5B). No replication of φul36 could be detected in *L. lactis* SMQ-88 whereas significant replication occurred in SMQ-86. The intracellular production of φul36 major capsid protein was also followed on SMQ-86 and SMQ-88 (FIG. 5C). The MCP is the most abundant structural protein of φul36 (Moineau, S., et al., Appl. Environ. Microbiol. 59:2034–2040 (1993)). Using an ELISA detection system, barely no MCP protein was detected in infected SMQ-88 cells (O.D.=0.389) whereas massive amount of MCP was detected in infected SMQ-86 cells (corrected O.D.=22.618). These results indicated that AbiE might act at or prior to phage DNA replication.

RESULTS

As can be seen from Examples 1 and 2, *Lactococcus lactis* subsp. lactis strain W1 harbors a 8.0-kb plasmid (pSRQ800) coding for a temperature-sensitive abortive phage infection mechanism. The genetic element responsible for the Abi+ phenotype was cloned and sequenced from pSRQ800. One gene was necessary for the Abi$^+$ phenotype.

AbiE displayed the classical abortive infection phenotype (Molineux, I. J., New Biol. 3:230–236 (1991); Sing, W. D., et al., J. Dairy Sci. 73:2239–2251 (1990); and Snyder, L., Mol. Microbiol. 15:415–420 (1995)). The presence of pSRQ800 increased the survival of infected cells by almost 50-fold demonstrating that AbiE was successful in aborting phage infection. Substantial cell death (98%) still occurred upon phage abortion (Table 5) suggesting that cell damage was too considerable for recovery. Very few infected AbiE$^+$ cells released progeny phages (0.5%) and when these rare productive infections occurred, the latent period was longer (by 15 min) and the burst size reduced by 15-fold. The overall effect of AbiE can be visualized as a reduction in number and size of phage plaques. Thus, AbiE acted internally to interfere with the phage lytic development.

AbiE encoded on its natural plasmid pSRQ800, inhibited the development of small isometric phages of the 936 and P335 species but had very limited effect on the prolate c2 species (Table 3). However if the abiE gene was cloned into the high copy vector pNZ123, a 4 log increase in resistance was noticed against phage φc2. This indicated that AbiE can be efficient against prolate phages when present in high copy number. A 2 log increase was also observed with φp2 (Table 3). Elevated efficiencies with high copy genes has also been observed with L. lactis AbiA (Casey, J., et al., Appl. Environ. Microbiol. 58:3283–3291 (1992); and Dinsmore, P. K., et al., Appl. Environ. Microbiol. 60:1129–1136 (1994)). Therefore, the natural plasmid pSRQ800 can bestow strong resistance against small isometric phages (936 and P335 species) and if the functional gene is delivered in an appropriate vector, AbiE can be effective against all three common lactococcal phage species (Jarvis, A. W., et al., Intervirology 32:2–9 (1991)).

Five other L. lactis Abi systems have been sequenced (Anba, J., et al., J. Bacteriol. 177:3818–3823 (1995); Cluzel, P. J., et al., Appl. Environ. Microbiol. 57:3547–3551 (1991); Durmaz, E., et al., J. Bacteriol. 174:7463–7469 (1992); Hill, C., et al., Appl. Environ. Microbiol. S6:2255–2258 (1990); and McLandsborough, L. A., et al., Appl. Environ. Microbiol. 61:2023–2026 (1995)). In all cases, only one gene was necessary to confer the Abi+ phenotype. The five deduced Abi proteins had 628 (AbiA), 251 (AbiB), 344 (AbiC), 366 (AbiD), and 351 (AbiD1) amino acids. Thus, AbiE (599 aa, 71.4-kDa) would be closer to AbiA (628 aa and 73.8 kDa) based on protein size.

Figure 5D:
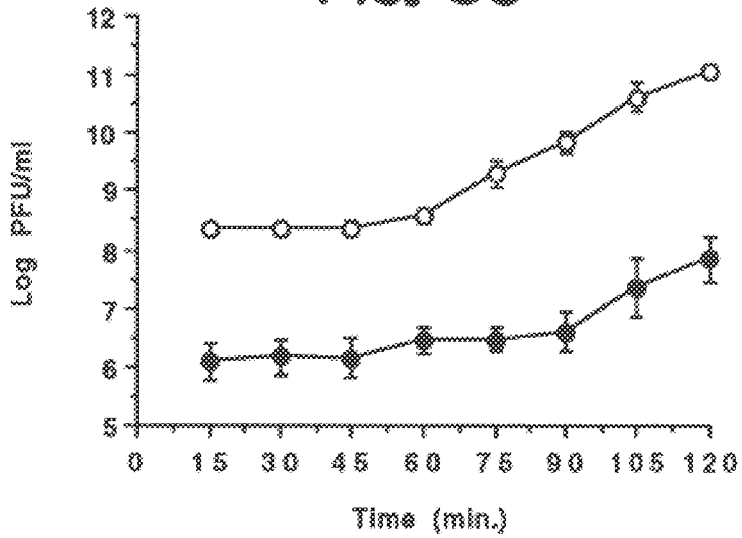
FIG. 5D is a graph showing one-step growth curves for φul36 on *L. lactis* SMQ-86 and SMQ-88. The phages were allowed to adsorb to the cells for 5 min., cells were washed twice to remove non-adsorbed phages and then resuspended in LM17 and incubated at 30° C. Time 15 min corresponded to the first phage count after resuspension in LM17. There was much more progeny phage released from SMQ-86.

Functionally, AbiE was also similar to AbiA. This was evidenced by its efficient inhibition of 936 and P335 species (Casey, J., et al., Appl. Environ. Microbiol. 58:3283–3291 (1992); Dinsmore, P. K., et al., Appl. Environ. Microbiol. 60:1129–1136 (1994); and Hill, C., et al., Appl. Environ. Microbiol. 56:2255–2258 (1990)), its increased activity against prolate phages with high copy (Casey, J., et al., Appl. Environ. Microbiol. 58:3283–3291 (1992); and Dinsmore, P. K., et al., Appl. Environ. Microbiol. 60:1129–1136 (1994)) and is heat sensitivity (Hill, C., et al., Appl. Environ. Microbiol. 56:2255–2258 (1990)). The AbiA phage target is currently unknown but it is believed to act prior to φ DNA replication since no DNA replication and MCP production were observed in infected AbiA+ cells (Moineau, S., et al., Appl. Environ. Microbiol. 59:208–212 (1993)). Similar DNA replication and MCP production results were obtained with AbiE (FIGS. 5C and 5D). Even though AbiE shared phenotypic similarities with AbiA, no significant amino acid homology was found between the two proteins.

When developing phage-resistant cultures, one approach is to stack different phage resistance mechanisms within one strain (Durmaz, E., et al., Appl. Environ. Microbiol. 61:1266–1273 (1995); and Sing, W. D., et al., Appl. Environ. Microbiol. 59:365–372 (1993)). In fact some natural L. lactis plasmids like pTR2030 (Hill, C., et al., Appl. Environ. Microbiol. 56:2255–2258 (1990); and O'Sullivan, D. J., et al., J. Bacteriol. 177:134–143 (1995)) and pTN20 (Durmaz, E., et al., J. Bacteriol. 174:7463–7469 (1992)), already encode two distinct phage resistance mechanisms: an abortive infection mechanism and a R/M system. In these two plasmids, the Abi and R/M systems naturally complement each other to confer very strong phage resistance (EOP $<10^{-9}$). AbiE and LlaDCHI are considered strong phage resistance mechanisms since EOPs of $10^{-6}$ were observed with some phages (Moineau, S., et al., Appl. Environ. Microbiol. 61:2193–2202 (1995), Table 3). However on their own, both systems are leaky and a high phage population ($>10^6$) can overpower them. When AbiE and LlaDCHI were introduced in L. lactis strains, a full resistance phenotype (EOP $<10^{-9}$) was observed against 936 and P335 phages (Table 4). These results demonstrated the beneficial effect of providing in trans an Abi and a R/M system. Similar added resistance have been previously observed with other in trans L. lactis anti-phage systems (Durmaz, E., et al., Appl. Environ. Microbiol. 61:1266–1273 (1995); and Sing, W. D., et al., Appl. Environ. Microbiol. 59:365–372 (1993)). This is believed to be the first instance where such a strong resistance is observed with completely characterized Abi and R/M systems presented in trans in L. lactis.

From a practical and current regulatory point of view, the introduction of the natural plasmid PSRQ800 into an industrial L. lactis strain to confer strong resistance against small-isometric phages of the 936 and P335 species, is useful. It is useful against c2 phage species when the AbiE gene is provided in large copy number.

The foregoing description is only illustrative of the present invention and the present invention is limited only by the hereinafter appended claims.

We claim:

1. An isolated DNA encoding a protein designated as AbiE contained in plasmid pSRQ800 which in a *Lactococcus lactis* increases resistance to phages by aborting infection of the *Lactococcus lactis* by phages.

2. An isolated DNA encoding a protein designated as AbiE in plasmid pSRQ800 as contained in *Lactococcus lactis* SMQ-20 deposited as NRRL-B-21443.

3. The DNA of claim 2 which is in a 4.5 kb EcoR1 segment contained in plasmid pSRQ800.

4. An isolated DNA having a nucleotide sequence as set forth in SEQ ID NO:1.

5. A recombinant plasmid containing DNA contained in plasmid *pSRQ800* encoding a protein designated as AbiE which in a *Lactococcus lactis* increases resistance to phages by aborting infection of the *Lactococcus lactis* by the phages.

6. The plasmid of claim 5 which is a shuttle vector pSA3 containing the DNA.

7. The plasmid of claim 5 which is pNZ123 containing the DNA.

8. The plasmid of claim 5 wherein the DNA is in plasmid pSRQ800 contained in *Lactococcus lactis* pSMQ-20 deposited as NRRL-B-21443.

9. A recombinant plasmid containing DNA having a nucleotide sequence as set forth in SEQ ID NO:1 which encodes a protein designated as AbiE.

10. The plasmid of claim 9 which is a shuttle vector pSA3 containing the DNA.

11. The plasmid of claim 9 which is pNZ123 containing the DNA.

12. A bacterium harboring a recombinant plasmid containing DNA contained in plasmid pSRO800 encoding a protein designated as AbiE which in a *Lactococcus lactis* increases resistance to phage by aborting infection of the *Lactococcus lactis* by the phages.

13. The bacterium of claim 12 which is a lactic acid producing bacterium selected from the group consisting of Lactococcus, Lactobacillus, Leuconostocs, Pediococcus, Streptococcus thermophilus, Enterococcus and Bifodobacterium.

14. The bacterium of claim 12 which is *Escherichia coli*.

15. The bacterium of claim 12 which is a *Lactococcus lactis*.

16. The bacterium of claim 12 harboring a shuttle vector pSA3 containing the DNA.

17. The bacterium of claim 12 harboring pNZ123 containing the DNA.

18. The bacterium of claim 12 wherein the DNA is contained in plasmid pSRQ800 contained in a *Lactococcus lactis* pSMQ-20 deposited as NRRL-B-21443.

19. A recombinant bacterium containing DNA having a nucleotide sequence as set forth in SEQ ID NO:1 which encodes a protein designated as AbiE which increases abortion of infection by phages.

20. The bacterium of claim 19 harboring a shuttle vector pSA3 containing the DNA.

21. The bacterium of claim 19 harboring PNZ123 containing the DNA.

22. A method of imparting phage resistance to a bacterium which is sensitive to the phage which comprises transferring DNA contained in pSRQ800 encoding a protein designated as AbiE which increases resistance to phages by aborting infection of Lactococcus lactis by the phages into the bacterium to impart the phage resistance.

23. The method of claim 22 wherein the DNA is contained in strain *Lactococcus lactis* SMQ-20 deposited as NRRL-B-21443.

24. The method of claim 22 wherein the DNA transferred is a shuttle vector pSA3.

25. The method of claim 22 wherein the DNA transferred is in pNZ123.

26. A method of claim 22 wherein a recombinant plasmid containing the DNA which has a nucleotide sequence as set forth in SEQ ID NO:1 which encodes the protein designated as ABiE is transferred.

27. A method of claim 26 wherein in the DNA transferred is in a shuttle vector pSA3.

28. A method of claim 26 wherein the DNA transferred is in pNZ123.

29. The method of claim 22 wherein the bacterium is a *Lactococcus lactis*.

30. The method of claim 22 wherein the DNA transferred is plasmid DNA.

31. The method of claim 22 wherein the DNA transferred is in a vector for transforming the bacterium.

32. *Lactococcus lactis* naturally lacking in phage resistance and containing transferred DNA encoding a protein designated as AbiE which increases resistance to phages by aborting infection of *Lactococcus lactis* by the phages, wherein the DNA comprises a sequence as set forth in SEQ ID NO:1 to impart phage resistance to the *Lactococcus lactis*.

33. The *Lactococcus lactis* of claim 32 wherein the DNA is contained in *Lactococcus lactis* SMQ-20 deposited as NRRL-B-21443.

34. The *Lactococcus lactis* of claim 32 wherein the DNA is in a plasmid.

35. The *Lactococcus lactis* of claim 32 wherein the DNA is in a vector for transformation.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 4467
        ( B ) TYPE: Nucleotide
        ( C ) STRANDEDNESS: Single
        ( D ) TOPOLOGY: Linear ( i i ) MOLECULE TYPE:
        ( A ) DESCRIPTION: Genomic DNA ( i i i ) HYPOTHETICAL: No ( i v ) ANTI-SENSE: No ( v ) FRAGMENT TYPE: N/A ( v i ) ORIGINAL SOURCE:
    ( A ) ORGANISM: Lactococcus lactis
    ( B ) STRAIN:
    ( C ) INDIVIDUAL ISOLATE: W1
    ( D ) DEVELOPMENTAL STAGE: N/A
    ( E ) HAPLOTYPE: N/A
    ( F ) TISSUE TYPE: N/A
    ( G ) CELL TYPE: bacterium
    ( H ) CELL LINE: N/A
    ( I ) ORGANELLE: N/A ( v i i ) IMMEDIATE SOURCE:
    ( A ) LIBRARY: genomic
    ( B ) CLONE: SMQ-20

( v i i i ) POSITION IN GENOME: N/A ( i x ) FEATURE:
    ( A ) NAME/KEY: phage abortive infection
    ( B ) LOCATION: N/A
    ( C ) IDENTIFICATION METHOD: sequencing
    ( D ) OTHER INFORMATION: DNA encoding phage
        resistance ( x ) PUBLICATION INFORMATION: N/A ( x i ) SEQUENCE DESCRIPTION: SEQ ID NO: 1:

```
GAATTCATGT  TTTGTTGGAT  GAGCCATGCA  TGATAAAGCA  TTAAATCTTG  TTGGACAGGT      60
TTTAAATATA  ACGTATTTCC  CTTACCTGTT  TTTTGATCAT  GAATAAATGC  AGTTTGTTTG     120
ACTGTTCCAT  CAAGATTAAA  GACATCTGTT  TTTTTAATT   TCATGACGTC  ACTCACACGT     180
AGCAAGGTCG  CTTTCCCAAC  TTGGAAAATT  GTATAGTTAC  GACGACCAGC  ACGAAAACTA     240
TCAAGTAGTG  TATCCTGCAC  CATTTTTAAG  ATATTTGAAT  CTTTAATCGG  TAAAACAAGT     300
TGTTGCACCA  TGATACTATT  GCTCCTTTAA  AATCAATTAA  TTGCTTATG   ATAGCAAATA     360
CGCTATCATA  ATAGTATGGA  AAAATTTGAG  TTTGATTATT  ACGATTGGGC  TGAATTTGAA     420
CAGTTCTTAG  ATCAGTTACC  TGATAAAGAT  GCTGCTAAGT  TAATTGCAAC  CATTCAAAAT     480
ATTGAAAATA  ATGGCCTCTT  AGTCGCTGAA  AGACAATTAT  GGGTCAAAAA  ACTAGAAAAT     540
AATCTTTATG  AAATTCGTTC  TAAGCGAGCT  TCAAACATCC  AAAGAGCGAT  TTATTTTAAA     600
GTCAAAGGTA  GTCAATACAT  TATTACTAAT  GCGTTCACGA  AAAAAACGCA  AAAGACACCT     660
GAAAATCAAA  AGGAAATTGC  TCGGAATAGA  CGCAGTCAGT  ATTTGAATAA  GGAGGAAAAC     720
CAATGAGTAA  ACTTGATGCA  TATGTTGCTG  AACGTAGTAA  AAAAAATCCC  AAATTTTCAC     780
AAATTGTTGA  GCAAGAAAAT  ATTAATTTAG  AGGTGGCAGT  AAAAGTCCAT  GACCTGCGTG     840
AAAATATGGG  GTTAAGTCAA  CGTGAATTTG  CTACTCTGAT  TGGTAAACCA  CAATCAACCA     900
TCGCACGCAT  TGAAAATGGT  TCGATGAATG  CTTCAACAAA  AATGTTATCA  GAGATTGCCC     960
AAGCTACTAA  TCAACGATTA  ACTATTCAAT  TTAATTCTAC  ATTTTAAGAT  CTATTATATC    1020
ATTTAACAAA  AAAATAGCCC  CTAATAAACC  AAAGTAATTT  ATTAGGGGCT  ATTTTAATAG    1080
TTTTTTAAAG  GGGTTATTTT  CTAATTATAG  TCCCTTAATT  TCCATTTTCG  TGTCTAATTA    1140
TTTGACATTA  GTCCATACAA  TAGTGACTCT  AAGATTTAAG  GATAACATCA  ACTTTCAACA    1200
TAAGCACAAT  AACTATTTTT  TTATTATAAT  TGAAAGAGA   ATTGAATTAT  TACCTATAAA    1260
ACTTAAAGGA  GTATAATT    ATG  AAA  AAA  GAG  TTT  ACT  GAA  TTA  TAT  GAT  1308
                       Met  Lys  Kys  Glu  Phe  Thr  Glu  Leu  Tyr  Asp
                                            5                         10

TTT  ATA  TTT  GAT  CCT  ATT  TTT  CTT  GTA  AGA  TAC  GGC  TAT  TAT  GAT  1353
Phe  Ile  Phe  Asp  Pro  Ile  Phe  Leu  Val  Arg  Tyr  Gly  Tyr  Tyr  Asp
```

|     |     |     |     | 15  |     |     |     |     | 20  |     |     |     |     | 25  |      |
| --- | --- | --- | --- | --- | --- | --- | --- | --- | --- | --- | --- | --- | --- | --- | ---- |
| AGA | TCT | ATT | AAA | ACC | AAA | AAA | ATG | AAT | CCT | CCA | AAA | GTT | GAA | TTA | 1398 |
| Arg | Ser | Ile | Lys | Thr | Lys | Lys | Met | Asn | Pro | Pro | Lys | Val | Glu | Leu |      |
|     |     |     |     | 30  |     |     |     |     | 35  |     |     |     |     | 40  |      |
| GAC | AAT | GAA | TAT | GGA | AAA | TCA | GAT | TCT | TTT | TAT | TTT | AAA | GTA | TTT | 1443 |
| Asp | Asn | Glu | Tyr | Gly | Lys | Ser | Asp | Ser | Phe | Tyr | Phe | Lys | Val | Phe |      |
|     |     |     |     | 45  |     |     |     |     | 50  |     |     |     |     | 55  |      |
| AAT | ATG | GAA | TCC | TTT | GCA | GAT | TAT | TTA | AGG | AGT | CAT | GAT | TTA | AAA | 1488 |
| Asn | Met | Glu | Ser | Phe | Als | Asp | Tyr | Leu | Arg | Ser | His | Asp | Leu | Lys |      |
|     |     |     |     | 60  |     |     |     |     | 65  |     |     |     |     | 70  |      |
| ACA | CAT | TTT | AAC | GGT | AAA | AAA | CCT | CTA | TCA | ACA | GAC | CCA | GTA | TAT | 1533 |
| Thr | His | Phe | Asn | Gly | Lys | Lys | Pro | Leu | Ser | Thr | Asp | Pro | Val | Tyr |      |
|     |     |     |     | 75  |     |     |     |     | 80  |     |     |     |     | 85  |      |
| TTT | AAT | ATT | CCA | AAA | AAT | ATA | GAA | GCT | AGA | AGA | CAA | TAT | AAG | ATG | 1578 |
| Phe | Asn | Ile | Pro | Lys | Asn | Ile | Glu | Ala | Arg | Arg | Gln | Tyr | Lys | Met |      |
|     |     |     |     | 90  |     |     |     |     | 95  |     |     |     |     | 100 |      |
| CCC | AAT | TTA | TAC | AGT | TAT | ATG | GCA | TTA | AAT | TAT | TAT | ATA | TGT | GAC | 1623 |
| Pro | Asn | Leu | Tyr | Ser | Tyr | Met | Ala | Leu | Asn | Tyr | Tyr | Ile | Cys | Asp |      |
|     |     |     |     | 105 |     |     |     |     | 110 |     |     |     |     | 115 |      |
| AAT | AAA | AAA | GAG | TTT | ATA | GAA | GTA | TTT | ATT | GAT | AAC | AAA | TTT | TCA | 1668 |
| Asn | Lys | Lys | Glu | Phe | Ile | Glu | Vla | Phe | Ile | Asp | Asn | Lys | Phe | Ser |      |
|     |     |     |     | 120 |     |     |     |     | 125 |     |     |     |     | 130 |      |
| ACG | TCA | AAA | TTT | TTT | AAT | CAA | TTG | AAT | TTT | GAT | TAT | CCT | AAG | ACA | 1713 |
| Thr | Ser | Lys | Phe | Phe | Asn | Gln | Leu | Asn | Phe | Asp | Tyr | Pro | Lys | Thr |      |
|     |     |     |     | 135 |     |     |     |     | 140 |     |     |     |     | 145 |      |
| CAA | GAA | ATT | ACA | CAA | ACA | TTA | TTA | TAT | GGA | GGA | ATA | AAG | AAA | TTA | 1758 |
| Gln | Glu | Ile | Thr | Gln | Thr | Leu | Leu | Tyr | Gly | Gly | Ile | Lys | Lys | Leu |      |
|     |     |     |     | 150 |     |     |     |     | 155 |     |     |     |     | 160 |      |
| CAT | TTA | GAT | TTA | TCT | AAT | TTT | TAT | CAT | ACT | TTA | TAT | ACA | CAT | AGT | 1803 |
| His | Leu | Asp | Leu | Ser | Asn | Phe | Tyr | His | Thr | Leu | Tyr | Thr | His | Ser |      |
|     |     |     |     | 165 |     |     |     |     | 170 |     |     |     |     | 175 |      |
| ATA | CCA | TGG | ATG | ATT | GAT | GGA | AAA | TCT | GCA | TCT | AAA | CAA | AAT | AGA | 1848 |
| Ile | Pro | Trp | Met | Ile | Asp | Gly | Lys | Ser | Ala | Ser | Lys | Gln | Asn | Arg |      |
|     |     |     |     | 180 |     |     |     |     | 185 |     |     |     |     | 190 |      |
| AAA | AAA | GGG | TTT | TCT | AAT | ACA | TTA | GAT | ACT | TTG | ATT | ACA | GCT | TGT | 1893 |
| Lys | Lys | Gly | Phe | Ser | Asn | Thr | Leu | Asp | Thr | Leu | Ile | Thr | Ala | Cys |      |
|     |     |     |     | 195 |     |     |     |     | 200 |     |     |     |     | 205 |      |
| CAA | TAC | GAC | GAA | ACA | CAT | GGC | ATT | CCA | ACT | GGA | AAT | CTA | TTG | TCT | 1938 |
| Gln | Tyr | Asp | Glu | Thr | His | Gly | Ile | Pro | Thr | Gly | Asn | Leu | Leu | Ser |      |
|     |     |     |     | 210 |     |     |     |     | 215 |     |     |     |     | 220 |      |
| AGG | ATT | ATT | ACC | GAA | CTA | TAT | ATG | TGC | CAT | TTT | GAT | AAA | CAA | ATG | 1983 |
| Arg | Ile | Ile | Thr | Glu | Leu | Tyr | Met | Cys | His | Phe | Asp | Lys | Gln | Met |      |
|     |     |     |     | 225 |     |     |     |     | 230 |     |     |     |     | 235 |      |
| GAA | TAT | AAG | AAG | TTT | GTG | TAT | TCA | AGA | TAT | GTA | GAT | GAT | TTT | ATA | 2028 |
| Glu | Tyr | Lys | Lys | Phe | Val | Tyr | Ser | Arg | Tyr | Val | Asp | Asp | Phe | Ile |      |
|     |     |     |     | 240 |     |     |     |     | 245 |     |     |     |     | 250 |      |
| TTT | CCG | TTT | ACT | TTT | GAG | AAT | GAA | AAG | CAA | GAA | TTT | TTA | AAT | GAA | 2073 |
| Phe | Pro | Phe | Thr | Phe | Glu | Asn | Glu | Lys | Gln | Glu | Phe | Leu | Asn | Glu |      |
|     |     |     |     | 255 |     |     |     |     | 260 |     |     |     |     | 265 |      |
| TTT | AAT | CTA | ATC | TGT | CGA | GAA | AAT | AAC | TTA | ATT | ATT | AAT | GAT | AAT | 2118 |
| Phe | Asn | Leu | Ile | Cys | Arg | Glu | Asn | Asn | Leu | Ile | Ile | Asn | Asp | Asn |      |
|     |     |     |     | 270 |     |     |     |     | 275 |     |     |     |     | 280 |      |
| AAA | ACG | AAA | GTT | GAC | AAT | TTC | CCG | TTT | GTT | GAT | AAA | TCG | AGT | AAA | 2163 |
| Lys | Thr | Lys | Val | Asp | Asn | Phe | Pro | Phe | Val | Asp | Lys | Ser | Ser | Lys |      |
|     |     |     |     | 285 |     |     |     |     | 290 |     |     |     |     | 295 |      |
| TCG | GAT | ATT | TTT | TCT | TTT | TTT | GAA | AAT | ATT | ACT | TCA | ACT | AAT | TCC | 2208 |
| Ser | Asp | Ile | Phe | Ser | Phe | Phe | Glu | Asn | Ile | Thr | Ser | Thr | Asn | Ser |      |
|     |     |     |     | 300 |     |     |     |     | 305 |     |     |     |     | 310 |      |
| AAC | GAC | AAG | TGG | ATT | AAA | GAA | ATA | AGC | AAT | TTT | ATA | GAT | TAT | TGT | 2253 |
| Asn | Asp | Lys | Trp | Ile | Lys | Glu | Ile | Ser | Asn | Phe | Ile | Asp | Tyr | Cys |      |

```
                                 315                         320                         325
GTG  AAT  GAA  GAA  CAT  TTA  GGG  AAT  AAG  GGA  GCT  ATA  AAA  TGT  ATT       2298
Val  Asn  Glu  Glu  His  Leu  Gly  Asn  Lys  Gly  Ala  Ile  Lys  Cys  Ile
                    330                         335                         340

TTC  CCA  GTT  ATA  ACA  AAT  ACA  TTG  AAA  CAA  AAA  AAA  GTA  GAT  ACT       2343
Phe  Pro  Val  Ile  Thr  Asn  Thr  Leu  Lys  Gln  Lys  Lys  Val  Asp  Thr
                    345                         350                         355

AAA  AAT  ATA  GAC  AAT  ATC  TTT  TCG  AAA  AGA  AAC  ATG  GTT  ACC  AAT       2388
Lys  Asn  Ile  Asp  Asn  Ile  Phe  Ser  Lys  Arg  Asn  Met  Val  Thr  Asn
                    360                         365                         370

TTT  AAT  GTT  TTC  GAA  AAA  ATA  TTA  GAT  TTA  TCA  TTA  AAA  GAT  TCA       2433
Phe  Asn  Val  Phe  Glu  Lys  Ile  Leu  Asp  Leu  Ser  Leu  Lys  Asp  Ser
                    375                         380                         385

AGA  TTA  ACT  AAT  AAG  TTT  TTG  ACT  TTC  TTT  GAA  AAT  ATT  AAT  GAA       2478
Arg  Leu  Thr  Asn  Lys  Phe  Leu  Thr  Phe  Phe  Glu  Asn  Ile  Asn  Glu
                    390                         395                         400

TTT  GGA  TTT  TCA  AGT  TTA  TCA  GCT  TCA  AAT  ATT  GTA  AAA  AAA  TAT       2523
Phe  Gly  Phe  Ser  Ser  Leu  Ser  Ala  Ser  Asn  Ile  Val  Lys  Lys  Tyr
                    405                         410                         415

TTT  AGT  AAT  AAT  TCA  AAG  GGC  TTA  AAA  GAA  AAA  ATA  GAC  CAC  TAT       2568
Phe  Ser  Asn  Asn  Ser  Lys  Gly  Leu  lys  Glu  Lys  Ile  Asp  His  Tyr
                    420                         425                         430

CGT  AAA  AAT  AAT  TTT  AAT  CAA  GAA  TTA  TAT  CAA  ATA  TTG  TTG  TAT       2613
Arg  Lys  Asn  Asn  Phe  Asn  Gln  Glu  Leu  Tyr  Gln  Ile  Leu  Leu  Tyr
                    435                         440                         445

ATG  GTT  GTC  TTT  GAA  ATA  GAT  GAT  TTA  TTA  AAT  CAA  GAA  GAA  TTA       2658
Met  Val  Val  Phe  Glu  Ile  Asp  Asp  Leu  Leu  Asn  Gln  Glu  Glu  Leu
                    450                         455                         460

CTA  AAC  TTA  ATT  GAT  TTA  AAT  ATT  GAT  GAT  TAT  TCT  TTA  ATT  TTA       2703
Leu  Asn  Leu  Ile  Asp  Leu  Asn  Ile  Asp  Asp  Tyr  Ser  Leu  Ile  Leu
                    465                         470                         475

GGG  ACG  ATT  TTA  TAC  CTA  AAG  AAT  AGT  TCA  TAT  AAA  TTG  GAA  AAA       2748
Gly  Thr  Ile  Leu  Tyr  Leu  Lys  Asn  Ser  Ser  Tyr  Lys  Leu  Glu  Lys
                    480                         485                         490

TTA  TTA  AAA  AAA  ATA  GAT  CAA  TTA  TTT  ATT  AAT  ACT  CAT  GCC  AAC       2793
Leu  Leu  Lys  Lys  Ile  Asp  Gln  Leu  Phe  Ile  Asn  Thr  His  Ala  Asn
                    495                         500                         505

TAC  GAC  TTG  AAA  ACT  TCT  CGT  ATG  GCA  GAA  AAA  TTA  TGG  CTA  TTT       2838
Tyr  Asp  Val  Lys  Thr  Ser  Arg  Met  Ala  Glu  Lys  Leu  Trp  Leu  Phe
                    510                         515                         520

CGT  TAT  TTC  TTT  TAT  TTT  TTA  AAT  TGT  AAG  AAT  ATT  TTT  AGT  CAA       2883
Arg  Tyr  Phe  Phe  Tyr  Phe  Leu  Asn  Cys  Lys  Asn  Ile  Phe  Ser  Gln
                    525                         530                         535

AAA  GAG  ATA  AAT  AGT  TAT  TGT  CAA  TCT  CAA  AAC  TAT  AAT  TCA  GGA       2928
Lys  Glu  Ile  Asn  Ser  Tyr  Cys  Gln  Ser  Gln  Asn  Tyr  Asn  Ser  Gly
                    540                         545                         550

CAG  AAC  GGA  TAT  CAA  ACA  GAA  CTT  AAT  TGG  AAT  TAT  ATT  AAA  GGT       2973
Gln  Asn  Gly  Tyr  Gln  Thr  Glu  Leu  Asn  Trp  Asn  Tyr  Ile  Lys  Gly
                    555                         560                         565

CAA  GGG  AAG  GAT  CTT  AGA  GCG  AAT  AAC  TTT  TTT  AAT  GAA  TTG  ATA       3018
Gln  Gly  Lys  Asp  Leu  Arg  Ala  Asn  Asn  Phe  Phe  Asn  Glu  Leu  Ile
                    570                         575                         580

GTA  AAA  GAA  GTT  TGG  TTA  ATT  TCT  TGT  GGT  GAG  AAC  GAA  GAT  TTC       3063
Val  Lys  Glu  Val  Trp  Leu  Ile  Ser  Cys  Gly  Glu  Asn  Glu  Asp  Phe
                    585                         590                         595

AAA  TAT  TTA  AAT  TGA  TA  AGTATTTGAA  ATCTATTATT  AGTTCCTGAA  AAAATAGCTG     3120
Lys  Tyr  Leu  Asn

TGTCTTGTCA  ATATAAATGA  CAAGACACAG  CTATTTTTTT  TAATTTTGAA  ATTTATAATT        3180

TTAAATGAAC  ATTTTTTGTA  AGAAACCTTT  TTTCTGTTCT  TTCAATAAAT  CTAATTTCCG        3240
```

-continued

| | | | | | | |
|---|---|---|---|---|---|---|
| CTGATGAAGA | GCGATAGTGT | CATCTAGCTG | TTTAAAGAAT | GAACCTATTT | TTTGTTGCTC | 3300 |
| TGAATTATTC | TGAGGAATCG | ATAGCTTCAG | TTCAGTCAAC | ATGTCCATAA | CAATGTACGG | 3360 |
| AATATTTCCT | GTACGAGCTT | CCTGTTTTAT | TTTTTAGGC | AGCTTATTTC | CAATTTCTGA | 3420 |
| AAATATAAAA | CTTCTATCTA | CTAGAAACTC | TTGGAGCACA | TAAGTTCGTT | GATAGGCATT | 3480 |
| GAACTTATTA | TCCGGCTAAA | TGCATGTATC | CAACTGTTGC | TCCATTACCT | GCAATTGTAA | 3540 |
| TGGACGGTCC | TTCAAACGCT | GCTACATCGA | TCCTATATTT | TTTAATTCCA | GAAGTATAAA | 3600 |
| AATCATACTT | GCCATTTTCA | ACCATTGCAT | TTGCATCTAA | TTTTCCGGTG | CTTATTTTAG | 3660 |
| TAATATCTCC | TAACTTACGC | TCTTCCCAAT | CGTCAGCAAA | CCCCGCAAAT | CGCAATTCAG | 3720 |
| GAACTTTAGC | CCCATTTTTA | GGGAACATTT | TTTGTAAGAA | GCCTTTTTC | TGTTCCTTGA | 3780 |
| GCAAATCTAA | CTTACGCTGA | TGAAGAGCGA | TAGTGTTATC | CAGCTGCTTG | AAGAATGAAC | 3840 |
| CGATTTTGTC | TTGTTCCTCA | ATTGCAGGGA | CACTTATTAT | AGCTTCTTTA | ATATCAGTAG | 3900 |
| AATTAATACT | TTCAAATGTT | GATCCAGTGC | TATATCTAGT | CCAATACCCG | TCGGACTTCA | 3960 |
| TTTTACCAAG | ATTTTGAAAT | ATAAATTCAT | TACCTTTTAT | GGCAGCAACA | CCTCGACCAA | 4020 |
| TAACAACGTC | ATAAGCTGTT | TTACCAATAT | CTCCAACCGG | TGCTCGGACA | CTTAGAATGA | 4080 |
| GATCATCTTT | TTCAGCTTGT | TTAGTAACTT | GAGTTGTCCA | TACTCTCGGT | AAAACACGAC | 4140 |
| CATTTTTCAT | GTCAGCATTA | CCTTGCACAA | GAATATAATC | ATTAGGATCA | TCAGTATAAT | 4200 |
| TTTCTGAATT | AGGAGACTGT | CCCATCACTA | TTCGAACTTC | GTCTCCCAAC | TTACGCAGTT | 4260 |
| CCCATTCATC | CGTGAATCCT | TTAAATCGCA | ATTCTGGAAC | TTTCTTTTTA | ACTGAATCAT | 4320 |
| CTATTTTCGC | CATAGTCCCC | ACCATTTTCT | TGGTTTTTCT | TGTTCTTCTA | TCCTTTTTTG | 4380 |
| ATCTTTGATT | TGTTCCTGCA | AATTTTCCAA | CTTCTCTTTA | AGAGCGTTCA | CTTCATCTTT | 4440 |
| ATATTGATTG | TCTAAGTGTT | TGAATTC | | | | 4467 |